US007711490B2

(12) United States Patent
Maranas et al.

(10) Patent No.: US 7,711,490 B2
(45) Date of Patent: May 4, 2010

(54) METHOD AND SYSTEM FOR MODELING CELLULAR METABOLISM

(75) Inventors: Costas D. Maranas, Port Matilda, PA (US); Anthony P. Burgard, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 4 days.

(21) Appl. No.: 10/043,440

(22) Filed: Jan. 10, 2002

(65) Prior Publication Data

US 2002/0168654 A1 Nov. 14, 2002

Related U.S. Application Data

(60) Provisional application No. 60/260,713, filed on Jan. 10, 2001, provisional application No. 60/278,535, filed on Mar. 23, 2001.

(51) Int. Cl.
*G06F 19/00* (2006.01)
*G06G 7/58* (2006.01)
(52) U.S. Cl. ......................................... 702/19; 703/11
(58) Field of Classification Search .................... 703/2, 703/11; 702/19
See application file for complete search history.

(56) References Cited

U.S. PATENT DOCUMENTS

| 4,520,103 | A | 5/1985 | Ensley, Jr. | |
|---|---|---|---|---|
| 2002/0012939 | A1* | 1/2002 | Palsson | 435/6 |
| 2002/0142321 | A1 | 10/2002 | Palsson et al. | |
| 2002/0168654 | A1 | 11/2002 | Maranas et al. | |
| 2003/0073092 | A1 | 4/2003 | Maranas et al. | |
| 2004/0009466 | A1 | 1/2004 | Woehr et al. | |
| 2005/0079482 | A1 | 4/2005 | Maranas et al. | |

FOREIGN PATENT DOCUMENTS

| JP | 2000-268018 | 3/1999 |
|---|---|---|
| WO | WO 98/18814 | 5/1998 |
| WO | WO 00/18906 | 4/2000 |
| WO | WO 00/42559 | 7/2000 |
| WO | WO 01/90346 | 11/2001 |
| WO | WO 02/055995 A2 | 7/2002 |
| WO | WO 04/018621 | 4/2004 |

OTHER PUBLICATIONS

Hatzimanikatis et al. AIChE Journal (May 1006) vol. 42, No. 5, pp. 1277-1292.*
Varma et al. (Applied and Environmental Microbiology (1994) vol. 60, No. 10. pp. 3724-3731.*
"Linear Programming Frequently Asked Questions", Optimization Technology Center of Northwestern University and Argonne National Laboratory. Found at www.unix.mcs.anl.gov/otc/Guide/faq/linear—programming—faq.html, Dec. 1, 2001.

"Metabolic flux balance analysis and the in silico analysis of *Escherichia coli* K-12 gene deletions" BMC Bioinformatics, vol. 1:1, pp. 1-10 Jeremy S. Edwards and Bernhard O. Palsson, (Jul. 27, 2000).
"Appendix 1: Flux balance analysis primer" from www.che.udel.edu/edwardsgroup/LAB/NBT_ExpPhPP/FBAprimer. Printed Jan. 4, 2002.
"Genetic and Metabolic engineering", EJB Electronic Journal of Biotechnology, vol. 1 (3), pp. 1-10. Yang et al. 1998.
Covert, "Regulation of Gene Expression in Flux Balance Models of Metabolism," J. Theor. Biol. 213, p. 73-88, (Nov. 7, 2001).
Edwards, "In silico predictions of *Escherichia coli* metabolic capabilities are consistent with experimental data," Nature Biotechnology, vol. 19 p. 125-130, (Feb. 2001).
Edwards, "The *Escherichia coli* MG1655 in silico metabolic genotype: Its definition, characteristics, and capabilities," PNAS, vol. 97 (No. 10), p. 5528-5533, (May 9, 2000).
Hatzimanikatis, "Analysis and Design of Metabolic Reaction Networks via Mixed-Integer Linear Optimization," AIChE Journal, vol. 42, (No. 5) p. 1277-1292, (May 1996).
Pramanik, "Stoichiometric Model of *Escherichia coli* Metabolism: Incorporation of Growth-Rate Dependent Biomass Composition and Mechanistic Energy Requirements," Biotechnology And Bioengineering, vol. 56, (No. 4) p. 398-421, (Nov. 4, 1997).
Varma,"Metabolic Capabilities of *Escherichia coli*: J. Synthesis of Biosynthetic Precursors and Cofactors," J. Theor. Biol. p. 477-502, (1993).
"The Challenges of in Silico Biology" Bernhard Palsson, 2000 Nature, Biotechnology vol. 18, pp. 1147-1150.
"How Will Bioinformatics Influence Metabolkic Engineering" Jeremy S. Edwards, Bernhard O. Palsson, Biotech. and Bioeng. vol. 58(2-3) pp. 162-169, (1998).
"[309d]—Tightening Flux Balance Models Through Boolean Relations", Anthony P. Burgard, Costas D. Maranas, AIChE Technical Program Menu from Genomics to Pathways #2.
"The Underlying Pathway Structure of Biochemical Reaction Networks", Christophe H. Schilling and Bernhard O. Palsson, 1998 PNAS, vol. 95, pp. 4193-4198.
"Combining Pathway Analysis with Flux Balance Analuysis for the Comprehensive Study of Metabolic Systems" Christophe H. Schilling, Jeremy S. Edwards, David Letscher, Bernhard O. Palsson; 2001 Biotech. & Bioeng. vol. 71 (4), pp. 287-306.
Anandalingam and Friesz, "Hierarchical Optimization: An Introduction," Annals. Ops. Res. 34:1-11 (1992).
Arigoni, et al., "A genome-based approach for the identification of essential bacterial genes," Nat. Biotechnol. 16 (9):851-856 (1998).

(Continued)

*Primary Examiner*—Lori A Clow
(74) *Attorney, Agent, or Firm*—McKee, Voorhees & Sease, P.L.C.

(57) ABSTRACT

This invention relates to methods and systems for in silico or bioinformatic modeling of cellular metabolism. The invention includes methods and systems for modeling cellular metabolism of an organism, comprising constructing a flux balance analysis model, and applying constraints to the flux balance analysis model, the constraints selected from the set consisting of: qualitative kinetic information constraints, qualitative regulatory information constraints, and differential DNA microarray experimental data constraints. In addition, the present invention provides for computational procedures for solving metabolic problems.

34 Claims, 26 Drawing Sheets

OTHER PUBLICATIONS

Aristidou et al., "Modification of central metabolic pathway in Escherichia coli to reduce acetate accumulation by heterolgous expression of the Bacillus subtilis acetolactate synthase gene," Biotechnol. Bioeng. 44:944-951 (1994).

Arita, "The metabolic world of Escherichia coli is not small," Proc. Natl. Acad. Sci. USA 101(6):1543-1547 (2004).

Arita, "Metabolic construction using shortest paths," Sim. Pract. Theory, 8(1-2):109-125 (2000).

Badarinarayana, et al., "Selection analyses of insertional mutants using subgenic-resolution arrays," Nat. Biotechnol. 19(11):1060-1065 (2001).

Bailey and Gribskov, "Combining evidence using p-values: application to sequence homology searches," Bioinformatics 14(1):48-54 (1998).

Bhaskar, et al., "Applications of Multiobjective Optimization in Chemical Engineering," Rev. Chem. Eng. 16(1):1-54 (2000).

Biebl, et al., "Microbial production of 1,3-propanediol propanediol," Appl. Microbiol. Biotechnol. 52(3):289-297 (1999).

Blattner, et al., "The complete genome sequence of Escherichia coli K-12," Science 277(5331):1453-74 (1997).

Bogarad and Deem, "A hierarchical approach to protein molecular evolution," Proc. Natl. Acad. Sci. USA 96 (6):2591-2595 (1999).

Bond and Lovley, "Electricity production by Geobacter sulfurreducens attached to electrodes," Appl. Environ. Microbiol. 69(3):1548-1555 (2003).

Burgard and Maranas, "Optimization-based framework for inferring and testing hypothesized metabolic objective functions," Biotechnol. Bioeng. 82(6):670-677 (2003).

Burgard and Maranas, "Probing the performance limits of the Escherichia coli metabolic network subject to gene additions or deletions," Biotechnol. Bioeng. 74(5):364-375 (2001).

Burgard et al., "Minimal Reaction Sets for Escherichia coli Metabolism under Different Growth Requirements and Uptake Environments," Biotechnol. Prog. 17(5):791-797 (2001).

Burgard et al., "Optknock: A bilevel programming framework for identifying gene knockout strategies for microbial strain optimization," Biotechnol. Bioeng. 84(6):647-657 (2003).

Cameron et al., "Metabolic engineering of propanediol pathways," Biotechnol. Prog. 14(1):116-125 (1998).

Castellanos et al., "A modular minimal cell model: purine and pyrimidine transport and metabolism," Proc. Natl. Acad. Sci. USA 101(17):6681-6686 (2004).

Causey et al., "Engineering Escherichia coli for efficient conversion of glucose to pyruvate," Proc. Natl. Acad. Sci. USA 101(8):2235-2240 (2004).

Chen and Zhu, "Computer Program for Calculating the Melting Temperature of Degenerate Oligonucleotides Used in PCR or Hybridization," BioTechniques, 22:1158-1160 (1997).

Chistoserdova et al., "C1 transfer enzymes and coenzymes linking methylotrophic bacteria and methanogenic Archaea," Science 281(5373):99-102 (1998).

Cho et al., "Ethical considerations in synthesizing a minimal genome," Science 286:2087-2090 (1999).

Compagno et al., "Glycerol production in a triose phosphate isomerase deficient mutant of Saccharomyces cerevisiae," Biotechnol. Prog. 12(5):591-595 (1996).

Covert et al., "Metabolic modeling of microbial strains in silico," Trends Biochem. Sci. 26:179-186 (2001).

Covert and Palsson, "Transcriptional regulation in constraints-based metabolic models of Escherichia coli," J. Biol. Chem. 277(31):28058-28064 (2002).

Datta et al., "Technological and economic potential of poly(lactic acid) and lactic acid derivatives," FEMS Microbiol. Rev. 16:221-231 (1995).

David et al., "Reconstruction of the central carbon metabolism of Aspergillus niger," Eur J. Biochem. 270 (21):4243-4253 (2003).

Delgado and Liao, "Identifying Rate-Controlling Enzymes in Metabolic Pathways without Kinetic Parameters," Biotechnol. Prog. 7:15-20 (1991).

Demain, "Stunning achievements of industrial microbiology," ASM News 65:311-316 (1999).

Edwards et al., "How will bioinformatics influence metabolic engineering?," Biotechnol. Bioeng. 58(2-3):162-169 (1998).

Ellis et al., "The University of Minnesota Biocatalysis/Biodegradation Database: post-genomic data mining," Nucl. Acids. Res. 31(1):262-265 (2003).

Eppstein, "Finding the k Shortest Paths" in 35th IEEE Symp Foundations of Comp Sci, Santa Fe, pp. 154-165 (1994).

Fisher "The langragean relaxation method for solving integer programming," Manage. Sci. 27:1 (1981).

Forster, et al., "Genome-scale reconstruction of the Saccharornyces cerevisiae metabolic network," Genome Res. 13 (2):244-253 (2003).

Geoffrion "Lagrangean relaxation and its uses in integer programming," Mat. Program. Stud. 2:82 (1974).

Gupta and Clark, "Escherichia coli derivatives lacking both alcohol dehydrogenase and phosphotransacetylase grow anaerobically by lactate fermentation," J. Bacteriol. 171(7):3650-3655 (1989).

Hartlep et al., "Study of two-stage processes for the microbial production of 1,3 propanediol from glucose," Appl. Microbiol. Biotechnol. 60(1-2):60-66 (2002).

Hatzimanikatis, et al., "Application of mathematical tools for metabolic design of microbial ethanol production," Biotechnol. Bioeng. 58(2-3):154-161 (1998).

Heinrich and Rapoport, "A linear steady-state treatment of enzymatic chains. General properties, control and effector strength," Eur. J. Biochem. 42(1):89-95 (1974).

Henriksen et al., "Growth energetics and metabolic fluxes in continuous cultures of Penicillium chrysogenum," J. Biotechnol. 45:149-164 (1996).

Hugler et al., "Malonyl-coenzyme a reductase from Chioroflexus aurantiacus, a key enzyme of the 3-hydroxypropionate cycle for autotrophic CO(2) fixation," J. Bacteriol. 184(9):2404-2410 (2002).

Hutchinson et al., "Global transposon mutagenesis and a minimal Mycoplasma genome," Science 286 (5447):2165-2169 (1999).

Ibarra et al., "Escherichia coli K-12 undergoes adaptive evolution to achieve in silico predicted optimal growth," Nature 420(6912):186-189 (2002).

Itaya, "An estimation of minimal genome size required for life," FEBS Lett. 362(3):257-260 (1995).

Jorgensen et al., "Metabolic flux distributions in Penicillium chrysogenum during fed-batch cultivations," Biotechnol. Bioeng. 46(2):117-131 (1995).

Kacser and Burns, "The control of flux," Symp. Soc. Exp. Biol. 27:65-104 (1973).

Kanehisa et al., "The KEGG resource for deciphering the genome," Nucl. Acids Res. 32(Database issue):D277-80 (2004).

Kanehisa and Goto, "KEGG: kyoto encyclopedia of genes and genomes," Nucl. Acids Res. 28(1):27-30 (2000).

Karp et al., "The EcoCyc and MetaCyc databases," Nucl. Acids Res. 28(1):56-59 (2000).

Karp et al., "The EcoCyc Database," Nucl. Acids Res. 30(1):56-58 (2002).

Varma et al., "Biochemical production capabilities of Escherichia coli," Biotechnol. Bioeng. 42(1):59-73 (1993).

Varma et al., "Stoichiometric Interpretation of Escherichia coli Glucose Catabolism Under Various Oxygenation Rates.," Appl. Environ. Microbiol. 59(8):2465-2473 (1993).

Varner and Ramkrishna, "Metabolic engineering from a cybernetic perspective. 1. Theoretical preliminaries," Biotechnol. Prog. 15(3):407-425 (1999).

Varner and Ramkrishna, "Mathematical Models of Metabolic Pathways," Curr. Opin. Biotechnol. 10(2):146-150 (Apr. 1999).

Voit, "Optimization in Integrated Biochemical Systems," Biotechnol. Bioeng. 40(5):572-582 (1992).

Wang, et al., "Cadmium removal by a new strain Pseudomonas aeruginosa in aerobic culture," App. Environ. Microbiol. 63:4075-4078 (1997).

Xie and Wang, "Stoichiometric analysis of animal cell growth and its application in medium design," Biotechnol. Bioeng. 43(11):1164-1174 (1994).

Xie and Wang, "Applications of improved stochiometric model in medium design and fed-batch cultivation of animal cells in bioreactor," Cytotechnology 15(1-3):17-29 (1994).

Xie and Wang, "Energy metabolism and ATP balance in animal cell cultivation using a stoichiometrically based reaction network," Biotechnol. Bioeng. 52(5):591-601 (1996).

Xie and Wang, "Integrated approaches to the design of media and feeding strategies for fed-batch cultures of animal cells," Trends Biotechnol. 15(3):109-113 (1997).

Xie and Wang, "Material Balance Studies on Animal Cell Metabolism Using Stoichiometrically Based Reaction Network," Biotechnol. Bioeng. 52:579-590 (1996).

Yang, et al., "Metabolic Flux Analysis of Escherichia coli Deficient in the Acetate Production Pathway and Expressing the Bacillus subtilis Acetolactate Synthase," Met. Eng. (1999).

Zeikus, "Biotechnology of succinate acid production and markets for derived industrial products," Appl. Microbiol. Biotechnol. 51:545-552 (1999).

Zeng and Biebl, "Bulk chemicals from biotechnology: the case of 1,3-propanediol production and the new trends," Adv. Biochem. Eng. Biotechnol. 74:239-59 (2002).

Zhu et al., "Improving 1,3-propanediol from glycerol in a metabolically engineered Escherichia coli by reducing accumulation of sn-glycerol-3 —phosphate," Biotechnol. Prog. 18(4):694-699 (2002).

URL http://www.ilog.com/products/cplex/) accessed via the GAMS (Brooke, et al., (1998).

Chistoserdova, Ludmila et al., "Multiple Formate Dehydrogenase Enzymes in the Facultative Methylotroph Methylobacterium extorquens AM1 Are Dispensable for Growth on Methanol", Journal of Bacteriology, vol. 186(1), pp. 22-28, Jan. 2004.

Karp, P.D., "Integrated pathway/genome databases and their role in drug discovery", Trends in Biotechnology, 17 (7):275-281, 1999.

Moore, Gregory L. et al., "Modeling DNA Mutation and Recombination for Directed Evolution Experiments" J. Theor. Biol. (2000) 205, 483-503.

Price, Nathan D. et al., "Genome-Scale Models of Microbial Cells:Evaluating the Consequences of Constraints" REVIEWS vol. 2, 886-897, 2004, www.nature.com/reviews/micro.

Tigr, Genomes, Medicine, and the Environment conference, Oct. 16-18, 2006, 2 pages, The Institute for Genomic Research, http://www.tgr.org printed from Internet Sep. 18, 2009.

Karp et al., "Ecocyc: Encyclopedia of Escherichia coli genes and metabolism," Nuc. Acids Res. 27:(1)55-58 (1999).

Kataoka et al., "Studies of hydrogen production by continuous culture system of hydrogen-producing anaerobic bacteria," Wat. Sci. Tech. 36:41-47 (1997).

Kauffman et al., "Advances in flux balance analysis," Curr. Opin. Biology. London, GB, 14(5):491-496 (2003).

Klamt et al., "FluxAnalyzer: exploring structure, pathways, and flux distributions in metabolic networks on interactive flux maps," Bioinformatics 19(2):261-269 (2003).

Kompala et al., GT, "Cybernetic Modeling of Microbial Growth on Multiple Substrates," Biotechnol. Bioeng. 26 (11):1272-1281 (1984).

Korotkova et al., "Poly-beta-hydroxybutyrate biosynthesis in the facultative methylotroph methylobacterium extorquens AM1: identification and mutation of gap11, gap20, and phaR," J. Bacteriol. 184(22):6174-6181 (2002).

Krieger et al., "MetaCyc: a multiorganism database of metabolic pathways and enzymes," Nucl. Acids Res. 32 (Database issue), D438-D4342 (2004).

Lutz et al., "Creating multiple-crossover DNA libraries independent of sequence identity," Proc. Natl. Acad. Sci. USA 98 (20):11248-11253 (2001).

Majewski and Domach, "Simple constrained-optimization view of acetate overflow in Escherichia coli," Biotechnol. Bioeng. 35(7):732-738 (1990).

McShan et al., "PathMiner: predicting metabolic pathways by heuristic search," Bioinformatics, 19(13):1692-1698 (2003).

Menendez et al., "Presence of acetyl coenzyme A (CoA) carboxylase and propionyl-CoA carboxylase in autotrophic Crenarchaeota and indication for operation of a 3-hydroxypropionate cycle in autotrophic carbon fixation," J. Bacteriol. 181(4):1088-1098 (1999).

Methe et al., "Genome of Geobacter sulfurreducens: metal reduction in subsurface environments," Science 302 (5652):1967-9 (2003).

Misawa et al., "Production of beta-carotene in Zymomonas mobilis and Agrobacterium tumefaciens by introduction of the biosynthesis genes from Erwinia uredovora," Appl. Environ. Microbiol. 57(6):1847-1849 (1991).

Moore et al., "Predicting crossover generation in DNA shuffling," Proc. Natl. Acad. Sci. USA 98(6):3226-3231 (2001).

Moore and Maranas, "Modeling DNA Mutation and Recombination for Directed Evolution Experiments" J. Theor. Biol. 205(3):483-503 (2000).

Mushegian and Koonin, "A minimal gene set for cellular life derived by comparison of complete bacterial genomes," Proc. Natl. Acad. Sci. USA 93(19):10268-10273 (1996).

Nakamura and Whited, "Metabolic engineering for the microbial production of 1,3-propanediol," Curr. Opin. Biotechnol. 14(5):454-459 (2003).

Oh and Liao, "Gene expression profiling by DNA microarrays and metabolic fluxes in Escherichia coli," Biotechnol. Prog. 16(2):278-286 (2000).

Overbeek et al., "WIT: integrated system for high-throughput genome sequence analysis and metabolic reconstruction," Nucl. Acids. Res. 28(1):123-125 (2000).

Palsson, "The Challenges of in Silico Biology," Nat. Biotechnol. 18(11):1147-1150 (2000).

Papin et al., "Metabolic pathways in the post-genome era," Trends Biochem. Sci. 28(5):250-258 (2003).

Papoutsakis, "Equations and calculations for fermentations of butyric acid bacteria," Biotechnol. Bioeng. 26(2):174-187 (1984).

Pennisi, "Laboratory Workhorse Decoded," Science 277:1432-1434 (1997).

Pharkya et al., "Exploring the overproduction of amino acids using the bilevel optimization framework OptKnock," Biotechnol. Bioeng. 84(7):887-899 (2003).

Price et al, "Genome-scale Microbial in Silico Models: the Constraints-Based Approach," Trends Biotechnol. 21 (4):162-169 (2003).

Quackenbush et al., "The TIGR Gene Indices: analysis of gene transcript sequences in highly sampled eukaryotic species," Nucleic Acids Res. 29:159-165 (2001).

Ramakrishna et al., "Cybernetic Modeling of Growth in Mixed, Substitutable Substrate Environments: Preferential and Simultaneous Utilization," Biotechnol. Bioeng. 52(1):141-151 (1996).

Ramakrishna et al., "Flux-balance analysis of mitochondrial energy metabolism: consequences of systemic stoichiometric constraints," Am. J. Physiol. Reg. Integr. Comp. Physiol. 280(3):R695-704 (2001).

Reed et al., "An expanded genome-scale model of Escherichia coli K-12 (iJR904 GSM/GPR)," Genome Biol. 4(9):R54 (2003).

Richmond et al., "Genome-wide expression profiling in Escherichia coli K-12," Nucl. Acids Res. 27(19):3821-3835 (1999).

SantaLucia Jr., "A unified view of polymer, dumbbell, and oligonucleotide DNA nearest-neighbor thermodynamics," Proc. Natl. Acad. Sci. USA, 95(4):1460-1465 (1998).

Savageau, "Biochemical Systems Analysis," J. Theor. Biol. 25:365-369 (1969).

Schilling and Palsson, "Assessment of the metabolic capabilities of Haemophilus influenzae Rd through a genome-scale pathway analysis," J. Theor. Biol. 203(3):249-83 (2000).

Schilling, et al, "Combining pathway analysis with flux balance analysis for the comprehensive study of metabolic systems," Biotechnol. Bioeng. 71(4):286-306 (2000).

Schilling, et al., "Genome-scale metabolic model of Helicobacter pylon 26695," J. Bacteriol. 184(16):4582-4593 (2002).

Schilling et al., "Toward metabolic phenomics: analysis of genomic data using flux balances," Biotechnol Prog, 15:288-295 (1999).

Segre et al., "Analysis of optimality in natural and perturbed metabolic networks," Proc Natl. Acad. Sci. USA 99 (23):15112-15117 (2002).

Segre et al., "From annotated genomes to metabolic flux models and kinetic parameter fitting," Omics, 7(3):301-316 (2003).

Selkov, et al., "MPW: the Metabolic Pathways Database," Nucl Acids Res, 26(1):43-45 (1998).

Stols and Donnelly, "Production of succinic acid through NAD(+)-dependent malic enzyme in an Escherichia coli mutant," Appl. Environ. Microbiol. 63(7):2695-2701 (1997).

Sun, "Modeling DNA Shuffling," Ann. Conf. Res. Comp. Mol. Biol. Proc. Second. Ann. Intl Conf. Comp. Mol. Biol. p. 251-257 (1998).

Supplemental European Search Report, EP 0379 2962 dated Apr. 11, 2007.

Supplemental European Search Report, the Penn State Research Foundation, EP 04 78 2168 dated Jul. 1, 2009, 2 pages.

TIGR-Web site. TIGR microbial database http://www.tirg.org (2009).

Tomita, et al., "E-CELL: software environment for whole-cell simulation," Bioinformatics 15(1):72-84 (1999).

Tomita, "The E-Cell Project: Towards Integrative Simulation of cellular Processes," New Gen. Comput. 18:1-12 (2000).

Torres et al., "An Indirect Optimization Method for Biochemical Systems: Description of Method and Application to the Maximization of the Rate of Ethanol, Glycerol, and Carbohydrate Production in Saccharomyces cerevisiae," Biotechnol. Bioeng. 55(5):758-772 (1997).

Valdes et al., "Metabolic reconstruction of sulfur assimilation in the extremophile Acidithiobacillus ferrooxidans based on genome analysis," BMC Genomics 4:51 (2003).

Varma and Palsson, "Metabolic Capabilities of Escherichia coli: Ii. Optimal Growth Patterns," J. Theor. Biol. 165:503-522 (1993).

Varma and Palsson, "Metabolic Flux Balancing: Basic Concepts, Scientific and Practical Use," Biotechnol. 12:994-998. (1993).

* cited by examiner

MODEL PREDICTIONS OF MAXIMUM THEORETICAL YIELDS OF AMINO ACIDS FOR GROWTH ON GLUCOSE AND ACETATE

| | Maximum Theoretical Yield (mmol / per 10 mmol Glucose) | | | | Maximum Theoretical Yield (mmol / per 10 mmol Acetate) | | | |
|---|---|---|---|---|---|---|---|---|
| | Palsson '93 | Modified Keasling '97 | Universal Model | % Increase | Palsson '93 | Modified Keasling '97 | Universal Model | % Increase |
| Alanine | 20.00 | 20.00 | 20.00 | - | 3.93 | 5.29 | 5.29 | - |
| Arginine | 7.74 | 9.26 | 10.07 | 8.75% | 1.51 | 2.43 | 2.65 | 9.05% |
| Asparagine | 15.60 | 18.18 | 19.23 | 5.77% | 3.24 | 4.66 | 4.91 | 5.45% |
| Aspartate | 18.20 | 20.00 | 20.00 | - | 3.82 | 5.29 | 5.29 | - |
| Cysteine | 9.75 | 11.49 | 11.90 | 3.57% | 1.81 | 3.29 | 3.42 | 3.80% |
| Glutamate | 10.00 | 13.33 | 13.33 | - | 2.68 | 3.65 | 3.65 | - |
| Glutamine | 10.00 | 13.33 | 13.33 | - | 2.50 | 3.46 | 3.46 | - |
| Glycine | 20.00 | 35.33 | 35.33 | - | 3.94 | 9.00 | 9.00 | - |
| Histidine | 7.30 | 9.77 | 9.80 | 0.23% | 1.37 | 2.43 | 2.54 | 4.53% |
| Isoleucine | 7.34 | 8.00 | 8.07 | 0.91% | 1.44 | 2.13 | 2.13 | - |
| Leucine | 6.67 | 8.00 | 8.00 | - | 1.59 | 2.18 | 2.18 | - |
| Lysine | 7.84 | 8.45 | 8.45 | - | 1.55 | 2.18 | 2.18 | - |
| Methionine | 5.74 | 7.04 | 7.19 | 2.16% | 1.11 | 1.81 | 1.85 | 2.46% |
| Phenylalanine | 5.29 | 5.76 | 5.76 | - | 1.00 | 1.47 | 1.47 | - |
| Proline | 10.00 | 10.91 | 10.91 | - | 2.10 | 2.90 | 2.90 | - |
| Serine | 20.00 | 23.04 | 23.04 | - | 3.94 | 5.87 | 5.87 | - |
| Threonine | 12.30 | 15.00 | 15.00 | - | 2.50 | 3.91 | 3.91 | - |
| Tryptophan | 4.14 | 4.67 | 4.73 | 1.28% | 0.76 | 1.17 | 1.19 | 1.32% |
| Tyrosine | 5.48 | 6.03 | 6.03 | - | 1.03 | 1.54 | 1.54 | - |
| Valine | 10.00 | 10.00 | 10.00 | - | 1.96 | 2.67 | 2.67 | - |

Palsson '93:            *E. coli* model proposed by Palsson (1993)
Modified Keasling '97:    Modified Keasling (1997) *E. coli* model as described in text
Universal Model:        Modified Keasling (1997) *E. coli* model augmented with non-*E. coli* reactions compiled by the Kyoto Encyclopedia of Genes and Genomes
% Increase:            Between the modified Keasling (1997) model and the Universal model

*Fig. 9*

MODIFICATIONS TO THE PRAMANIK AND KEASLING MODEL*

| Enzymes | Reactions |
|---|---|
| Reactions assumed irreversible | |
| Phosphofructokinase | Fructose-1,6-bisphosphate → Fructose-6-phosphate + Pi |
| Citrate Synthase | Acetyl-CoA + Oxaloacetate → CoA + Citrate |
| 2-Ketoglutarate Dehydrogenase | 2-Ketoglutarate + NAD + CoA → Succinyl-CoA + $CO_2$ + NADH |
| PRSCAIM Synthetase | RCAIM + ATP + Aspartate → ADP + Pi + PRSCAIM |
| Glycerol Kinase | Glycerol + ATP → Glycerol-3-phosphate + ADP |
| Reactions removed from model | |
| Unknown Pathway | 5'-methylthioadenosine → Adenosine + Methionine |
| Cystathionase | Homocysteine + Adenosine ←→ s-Adenosyl-homocystine |
| Sulfotransferase | Adenosine-3,5-diphosphate + sulfite ←→ 3-Phosphoadenylylsulfate |
| Reactions modified | |
| Fructose-1,6-bisphosphate Aldolase | Fructose-1,6-bisphosphate → Fructose-6-phosphate + Pi |
| Isocitrate Dehydrogenase | Isocitrate + NADP ←→ $CO_2$ + NADPH + 2-Ketoglutarate |
| Succinate Thiokinase | Succinyl-CoA + ADP + Pi ←→ ATP + CoA + Succinate |
| Prephenate Dehydrogenase | Prephenate + NAD → $CO_2$ + NADH + para-Hydroxy phenyl pyruvate |
| Hol Dehydrogenase | Histidinol + 3 NAD → 3 NADH + Histidine |
| RCAIM Synthetase | AIR + $CO_2$ + ATP → 5-p-Ribosyl-4-carboxy-5-aminoimidazole + ADP + Pi |
| GTP Cyclohydrolase | GTP → D6RP5P + Formate + Ppi |
| 3,4-Dihydroxy-2-Butanone-4-Phosphate Synthase | Ribulose-5-phosphate → DB4P + Formate |
| H2Neopterin Triphosphate Pyrophosphatase | AHTD → PPi + Pi + DHP |
| CoA Synthase | OIVAL + METTHF + NADPH + ALA + CTP + 4 ATP + CYS → THF + NADP + AMP + 2 PPi + 2 ADP + $CO_2$ + CoA + CDP |

*MODIFICATIONS BASED ON INFORMATION BY KARP (1999)

Fig. 12

GENES SELECTED FOR REMOVAL BY KNOCKOUT STUDY

| Enzymes | Genes | Reactions |
| --- | --- | --- |
| 3,5-ADP Phosphatase | AP$^e$ | 35ADP → AMP + Pi |
| Acetate Kinase | ackA | AC + ATP → ACTP + ADP |
| CDP Kinase | ndk$^a$ | CDP + ATP → CTP + ADP |
| CMP Kinase | ndk$^b$ | CMP + ATP → CDP + ADP |
| F0F1-ATPase | unc | ADP + Pi + H$_{ext}$ → ATP |
| Formate THF Ligase | FTL$^c$ | THF + FORMATE + ATP → ADP + Pi + FTHF |
| Fumarase | fumAB | FUM → MAL |
| Glyceraldehyde Kinase | GK$^d$ | GLAL + ATP → ADP + T3P1 |
| Glycine Cleavage System | gcvHTP | GLY + THF + NAD → METTHF + NADH + CO2 + NH3 |
| Malate Dehydrogenase | mdh | MAL + NAD → NADH + OA |
| Methenyl THF Cyclohydrolase | folD$^f$ | METHF → FTHF |
| Methylene THF Dehydrogenase | folD$^g$ | METTHF + NADP → METHF + NADPH |
| NADH Dehydrogenase I | ndh | NADH + Q → NAD + QH2 + 4 H$_{ext}$ |
| PEP Synthase | pps | PYR + ATP → PEP + AMP + Pi |
| Phosphatidate Phosphatase | dgkA | DGR + Pi → PA |
| Phosphotransacetylase | pta | ACTP + COA → ACCOA + Pi |
| Pyrophosphatase | ppa | PPi → 2 Pi |
| Succinate Dehydrogenase | sdhABCD | SUCC + FAD → FADH2 + FUM |
| Succinate Thiokinase | sucCD | SUCCOA + GDP + Pi → GTP + COA + SUCC | a,b  Same gene responsible for two intracellular reactions
f,g  Same gene responsible for two intracellular reactions
c,d,e  No gene has been assigned to these intracellular reactions

*Fig. 14*

MODEL SELECTIONS OF ENZYMATIC REACTIONS THAT WILL
ENHANCE THE AMINO ACID PRODUCTION CAPABILITIES OF
*ESCHERICHIA COLI*

| Amino Acid | Substrate | EC# | Enyzme | Reaction Catalyzed |
|---|---|---|---|---|
| Arginine | Glucose: | 2.7.1.90 | 6-Phosphofructokinase (pyrophosphate) | Fructose-6-P + PPi → Fructose-1,6-Bisphosphate + Pi |
|  |  | 2.7.2.2 | Carbamate kinase | ATP + NH3 + CO2 → ADP + Carbamoyl Phosphate |
|  | Acetate: | 2.7.2.2 | Carbamate kinase | ATP + NH3 + CO2 → ADP + Carbamoyl Phosphate |
|  |  | 2.7.2.12 | Acetate kinase (pyrophosphate) | Acetate + PPi → Pi + Acetyl-Phosphate |
| Asparagine | Glucose/Acetate: | 6.3.1.4 | Aspartate—ammonia ligase (ADP-forming) | ATP + NH3 + L-Aspartate → Pi + ADP + L-Asparagine |
| Cysteine | Glucose/Acetate: | 2.7.7.5 | Sulfate adenylyltransferase (ADP) | Sulfate + ADP → Pi + Adenylyl-Sulfate |
| Histidine | Glucose: | 1.4.1.10 | Glycine dehydrogenase | NAD + glycine → glyoxylate + NADH + NH3 |
|  |  | 2.7.1.90 | 6-Phosphofructokinase (pyrophosphate) | Fructose-6-P + PPi → Fructose-1,6-Bisphosphate + Pi |
|  | Acetate: | 1.4.1.10 | Glycine dehydrogenase | NAD + glycine → glyoxylate + NADH + NH3 |
|  |  | 4.1.1.38 | Phosphoenolpyruvate carboxykinase (pyrophosphate) | PPi + Oxaloacetate → CO2 + Pi + PEP |
| Isoleucine | Glucose: | many |  |  |
| Methionine | Glucose: | 2.7.7.5 | Sulfate adenylyltransferase (ADP) | Sulfate + ADP → Pi + Adenylyl-Sulfate |
|  | Acetate: | 1.4.1.10 | Glycine dehydrogenase | NAD + glycine → glyoxylate + NADH + NH3 |
|  |  | 2.7.7.5 | Sulfate adenylyltransferase (ADP) | Sulfate + ADP → Pi + Adenylyl-Sulfate |
|  |  | 2.7.9.1 | Pyruvate,phosphate dikinase | Pyruvate + Pi + ATP → AMP + PPi + PEP |
|  |  | 4.1.1.38 | Phosphoenolpyruvate carboxykinase (pyrophosphate) | PPi + Oxaloacetate → CO2 + Pi + PEP |
| Tryptophan | Glucose: | 2.7.1.90 | 6-Phosphofructokinase (pyrophosphate) | Fructose-6-P + Ppi → Fructose-1,6-Bisphosphate + Pi |
|  |  | 2.7.9.1 | Pyruvate,phosphate dikinase | Pyruvate + Pi + ATP → AMP + PPi + PEP |
|  | Acetate: | 2.7.9.1 | Pyruvate,phosphate dikinase | Pyruvate + Pi + ATP → AMP + PPi + PEP |
|  |  | 4.1.1.38 | Phosphoenolpyruvate carboxykinase (pyrophosphate) | PPi + Oxaloacetate → CO2 + Pi + PEP |

*Fig. 15*

EVOLUTION OF MINIMAL REACTION SETS FOR CASE (I) UNDER DECREASING GROWTH REQUIREMENTS.

| Target % Maximum Growth Rate | Minimal Reaction Set (# Reactions) | Key Features |
|---|---|---|
| 100% | 234 | The glycolysis, tricarboxylic acid cycle, and pentose phosphate pathways are all operating in their forward directions, optimally generating the energy cofactors ATP, NADH, and NADPH required for cell growth. All available glucose is oxidized into the cell's only secreted byproduct, carbon dioxide. |
| 90% | 229 | The fluxes through two TCA cycle reactions 2-ketoglutarate dehydrogenase and succinate dehydrogenase are zero while succinyl-CoA synthetase operates in its reverse direction suggesting a less demanding energetic state under the sub-maximal growth demands. Acetate is now secreted as a byproduct along with carbon dioxide. |
| 80% | 228 | Fluxes through two additional TCA cycle reactions, fumarase and malate dehydrogenase, are eliminated while a reaction secreting fumarate is added. |
| 70% | 226 | The pentose phosphate pathway operates solely for nucleotide biosynthesis with the reaction fluxes through ribulose phosphate 3-epimerase, transketolase I, transketolase II, and transaldolase B all operating in reverse. Fluxes through glucose-6-phosphate dehydrogenase, lactonase, and 6-phosphogluconate dehydrogenase are absent in this case, replaced by pyridine nucleotide transhydrogenase which meets the cellular NADPH needs. In addition, formate is now secreted along with acetate, fumarate, and carbon dioxide. |
| 60%, 50%, 40% | 225 | Acetate is no longer secreted as a metabolic byproduct, but is converted to acetyl-CoA by acetyl-CoA synthetase. |
| 30%, 20%, 10%, 1% | 224 | Three glycolytic reactions, phosphoglycerate mutase, enolase, and pyruvate kinase are eliminated, but both serine deaminase and phosphoenolpyruvate synthase are added to supply the cell with phosphoenolpyruvate. |

*Fig. 22*

METABOLITES UPTAKEN OR SECRETED AT EACH TARGET GROWTH RATE ON AN OPTIMALLY ENGINEERED MEDIUM.
U – DENOTES METABOLITE UPTAKE
S – DENOTES METABOLITE SECRETION

| Metabolite | Percentage of 100% Biomass Generation Required | | | | | | | | | | | | |
|---|---|---|---|---|---|---|---|---|---|---|---|---|---|
| | 100% | 99.5% | 99% | 98% | 97% | 96% | 95% | 90% | 85% | 80% | 70% | 60% | 10% |
| Acetate | | | | | | | | | | | | S | S |
| Acetaldehyde | | | | | | | | | | | | | U |
| Adenine | | | U | U | U | U | U | U | | | U | | |
| Adenosine | | | | | | | | | | U | U | | U |
| Alanine | | | | | | | | | | U | U | | |
| Arginine | U | U | U | U | U | U | U | U | U | U | U | U | U |
| Asparagine | | | | | | | | | U | U | | U | U |
| Aspartate | | | | | | | | | U | U | U | U | U |
| Carbon dioxide | S | S | S | S | S | S | S | S | S | S | S | S | S |
| Cysteine | U | U | U | U | U | U | U | U | U | U | U | U | U |
| D-Alanine | | | | | | | | U | U | | | U | U |
| Thymidine | | U | U | U | U | U | U | U | U | U | U | U | U |
| Ethanol | U | U | U | U | U | U | U | U | | U | | U | |
| Glycerol | | | | | | | | | | | U | | |
| Glycerol-3-phosphate | U | U | U | U | U | U | U | U | U | U | | U | U |
| Glutamine | | | | | | | | | U | U | U | U | U |
| Glutamate | | | | | | | | | | | S | U | U |
| Glycine | | | | | | U | U | U | U | U | U | U | U |
| Guanine | | | U | U | U | U | | | U | U | | | |
| Guanosine | | | | | | | | U | | | U | U | U |
| Histidine | | U | U | U | U | U | U | U | U | U | U | U | U |
| Isoleucine | U | U | U | U | U | U | U | U | U | U | U | U | U |
| Leucine | | | | | | | U | U | U | U | U | U | U |
| Lysine | U | U | U | U | U | U | U | U | U | U | U | U | U |
| Meso-diaminopimelate | | U | U | U | U | U | U | U | U | U | U | U | U |
| Methionine | U | U | U | U | U | U | U | U | U | U | U | U | U |
| Mannitol | | | | | | | | | | | | U | U |
| Ammonia | U | U | U | U | U | U | U | U | | | | | |
| Oxygen | U | U | U | U | U | U | U | U | U | U | U | U | U |
| Phenylalanine | | | U | U | U | U | U | U | U | U | U | U | U |
| Phosphate | U | U | U | U | U | U | U | U | U | U | U | U | U |
| Proline | | | | U | U | U | U | U | U | U | U | U | U |
| Putrescine | U | U | U | U | U | U | U | U | U | U | U | U | U |
| Pyruvate | | | | | | | | | | U | U | U | U |
| Ribose | | | | | | | | | | | | U | U |
| Serine | | | | | | | | U | U | U | U | U | U |
| Spermidine | U | U | U | U | U | U | U | U | U | U | U | U | U |
| Threonine | | U | U | U | U | U | U | U | U | U | U | U | U |
| Tryptophan | | U | U | U | U | U | U | U | U | U | U | U | U |
| Tyrosine | | | U | U | U | U | U | U | U | U | U | U | U |
| Uracil | | | | | U | U | U | U | | | U | | |
| Uridine | | | | | | | | | | | U | U | U |
| Valine | | | | | | | U | U | U | U | U | | U |
| # Metabolites Uptaken | 12 | 17 | 19 | 21 | 22 | 24 | 26 | 28 | 29 | 31 | 29 | 34 | 34 |

*Fig. 23*

EVOLUTION OF MINIMAL REACTION SETS FOR CASE (II) UNDER DECREASING GROWTH REQUIREMENTS.

| Target % Maximum Growth Rate | Minimal Reaction Set (# Reactions) | Key Features |
|---|---|---|
| 100% | 201 | The organic material transported into the cell includes ethanol and glycerol-3-phosphate which fuel glycolysis, the TCA cycle, and PPP. The flux directions of the glycolysis pathway are split with all reaction fluxes preceding glyceraldehyde-3-phosphate (G3P) dehydrogenase operating in reverse, and all fluxes following and including G3P dehydrogenase operate in their forward directions. Putrescine, spermidine, and five amino acids are transported into the network eliminating the need for biosynthetic pathways for these components. |
| 90% | 132 | While the PPP and TCA cycle reactions are still functional, the network no longer utilizes the five glycolytic reactions from glyceraldehyde-3-phosphate dehydrogenase to pyruvate kinase. Consequently, the TCA cycle is completely fueled by imported ethanol and acetate rather than flux from the glycolysis pathway. |
| 80% | 125 | This network tolerates the complete elimination of the TCA cycle and glyoxylate shunt. As a result, the function of the pentose phosphate pathway reactions is no longer restricted to nucleotide biosynthesis, but now includes the formation of cellular NADPH. Most of this NADPH is subsequently converted to NADH by pyridine nucleotide transhydrogenase to replace the cellular reducing power lost from the inactivity of the TCA cycle. |
| 70% | 124 | A slightly less efficient set of internal metabolic reactions enables the growth demands to be met with the importation of one less metabolite (i.e. one less transport reaction) than its 80% counterpart. |
| 60% 50%, 40% 30%, 20% | 123 | Neither the TCA cycle nor PPP are utilized for reducing power. Most of the cellular reducing capabilities are now generated from the uptake of ethanol and its subsequent conversion into acetyl-CoA. |
| 10%, 1% | 122 | This minimal network is comprised mostly of cell envelope and membrane lipid biosynthetic reactions, along with a number of transport and salvage pathway reactions. Here, the three core metabolic routes, glycolysis, the TCA cycle, and the pentose phosphate pathway are almost completely dismantled with only one glycolytic and 4 PPP reactions remaining. |

*Fig. 26*

FUNCTIONAL CLASSIFICATION OF MINIMAL NETWORKREACTIONS FOR GROWTH ON AN OPTIMALLY ENGINEERED MEDIUM.

| Functional Classification | # rxns |
|---|---|
| ALA Isomerization | 1 |
| Alternative Carbon Source | 7 |
| Anaplerotic Reactions | 1 |
| Cell Envelope Biosynthesis | 29 |
| EMP Pathway | 5 |
| Membrane Lipid Biosynthesis | 16 |
| Pentose Phosphate Pathway | 4 |
| Pyrimidine Biosynthesis | 1 |
| Respiration | 5 |
| Salvage Pathways | 17 |
| Transport | 36 |
|  | 122 |

*Fig. 27*

| COMPARISON OF MINIMAL METABOLIC GENE/REACTION SETS BASED ON FUNCTIONAL CLASSIFICATION* | | | |
|---|---|---|---|
| Metabolic Function | Essential Gene Set[+] Ref. (2) | Minimal Gene Set Ref. (5) | Minimal Reaction Set |
| | # Genes | # Genes | # Reactions |
| Amino acid biosynthesis | 0 | 0 | 1 |
| Biosynthesis of cofactors, prosthetic groups, and carriers | 4 | 3 | 0 |
| Cell envelope | 2 | 11 | 29 |
| Central intermediary metabolism | 7 | 7 | 1 |
| Energy metabolism | 31 | 32 | 21 |
| Fatty acid and phospholipid metabolism | 5 | 7 | 16 |
| Purines, pyrimidines, nucleosides, and nucleotides | 17 | 14 | 18 |
| Transport and binding proteins | 17 | 25 | 36 |
| | 83 | 99 | 122 |

*Fig. 28*

METHOD AND SYSTEM FOR MODELING CELLULAR METABOLISM

PRIORITY STATEMENT

This application claims benefit of Provisional Patent Application No. 60/260,713 filed Jan. 10, 2001 and Provisional Patent Application No. 60/278,535 filed Mar. 23, 2001, both of which are herein incorporated by reference in their entirety.

FIELD OF THE INVENTION

This invention relates to methods and systems for in silico or bioinformatic modeling of cellular metabolism. More specifically, although not exclusively, this invention relates to a framework of models and methods that improve upon flux balance analysis (FBA) models through incorporation of particular constraints. These constraints incorporate, without limitation, qualitative kinetic information, qualitative regulatory information, and/or DNA microarray experimental data. Further, the present invention relates to solving various metabolic problems using particular computational procedures.

BACKGROUND OF THE INVENTION

Metabolic pathway engineering has attracted significant interest in recent years catalyzed by the rapidly increasing number of sequenced microbial genes. As of January 2001, over fifty microbial genomes were completely sequenced. Bioinformatic tools have allowed the functional assignment of 45 to 80% of their coding regions. E. Pennisi, Science 277, 1432 (1997). This newly acquired information is used in conjunction with microbial mathematical models to calculate the response of metabolic networks after gene knockouts or additions. For example, such information was used to increase ethanol production in metabolically engineered $E.$ $coli$ cells. V. Hatzimanikatis, et al., Biotechnol. Bioeng. 58, 154 (1998).

In general, mathematical models of cellular metabolism fall into two distinct categories, ones that incorporate kinetic and regulatory information and others that include only the stoichiometry of the reaction pathways. The first class of models matches cellular behavior at an original steady state and then employs kinetic and regulatory relations to examine how the cell behaves away from this steady state in the presence of small perturbations brought about by environmental changes or enzyme engineering. The key advantage of this first class of methods is that upon application a unique point in the metabolite flux space is identified. The disadvantage is that the required kinetic parameters are difficult to estimate and their accuracy and reproducibility may deteriorate rapidly as the system moves far away from the original steady-state.

The second class of models, flux balance analyses, utilizes only the stoichiometric mass balances of the metabolic network and cellular composition information, in the absence of detailed kinetic and thermodynamic data, to identify boundaries for the flux distributions available to the cell. Although microorganisms have evolved highly complex control structures that eventually collapse these available boundaries into single points, flux balance models are still valuable in setting upper bounds for performance targets and in identifying "ideal" flux distributions.

However, the versatility of flux balance analysis comes at the expense of unknowingly crossing kinetic or regulatory flux barriers. Flux balance model predictions must thus be cautiously interpreted as "ideal" flux distributions yielding upper bounds to the performance of the metabolic network. The key advantage of flux balance models is that, by not requiring any numerical values for kinetic parameters or regulatory loops, they are straightforward to compile. The key disadvantage is that the obtained stoichiometric boundaries can be very wide and it is hard to envision that the biomass maximization conjecture, while useful under certain conditions, is generally applicable.

It is therefore a primary object of the present invention to provide a method and system that improves upon the state of the art.

It is a further object of the present invention to provide a method and system that provides a framework for improving upon flux balance analysis models.

It is a still further object of the present invention to provide a method and system that allows the predictive capabilities of flux balance analysis models to be enhanced.

Another object of the present invention is to provide a method and system that incorporates qualitative kinetic and/or regulatory information into a flux balance analysis model.

Yet another object of the present invention is to provide a method and system that incorporates differential DNA microarray experimental data into a flux balance analysis model.

A further object of the present invention is to provide an improved method and system for determining minimal reaction sets for growth.

Another object of the present invention is to provide an improved method and system for determining the effect of environmental conditions on minimal reaction sets.

It is another object of the present invention to provide a method for calculating the response of metabolic networks after gene knockouts or additions.

A still further object of the present invention is to provide a method and system for selecting mathematically optimal genes for recombination.

Another object of the present invention is to provide a method and system for identifying lethal gene deletions.

Yet another object of the present invention is to provide a method and system for identifying gene therapeutic candidates for pathogenic microbes.

A still further object of the present invention is to provide a method and system capable of testing hypotheses or objective functions.

These and other objects, features and/or advantages of the present invention will become apparent from the specification and claims.

SUMMARY OF THE INVENTION

This invention includes a framework for in silico or bioinformatic modeling of cellular metabolism. The framework allows for an improvement to FBA models through incorporation of particular constraints. Preferably, these constraints are logic constraints that can be represented with binary variables. The framework provides for applying computational procedures in order to solve for model predictions. The model can be used to determine: how many and which foreign genes should be recombined into an existing metabolic network; which regulatory loops should be activated or inactivated so that a given metabolic target is optimized; how robust is a metabolic network to gene deletion; what is the mathematically minimal set of genes capable of meeting certain growth demands for a given uptake environment; whether experimental flux data, under different substrates and carbon/oxygen uptake rates, are consistent with different hypothesized objective functions; and other metabolic problems. The results obtained from use of this framework can be applied in a number of areas of research or commercial interest related to metabolic engineering, including areas in the biological, chemical, pharmaceutical, life sciences, and medical fields.

BRIEF DESCRIPTION OF THE DRAWINGS

FIG. 9 is a table of model predictions for maximum theoretical yields of seven amino acids for growth on glucose and acetate.

FIG. 10 shows the difference between optimal E. coli and Universal arginine production pathways for growth on glucose, including (a) the pyrophosphate dependent analog of 6-phosphofructokinase in the Universal model replacing the ATP dependent version present in E. coli; and (b) carbamate kinase in the Universal model replacing carbamoyl phosphate synthetase from the E. coli network.

FIG. 12 is a table showing modifications to the Pramanik and Keasling model.

FIG. 14 is a table showing genes selected for removal by knockout study.

FIG. 15 is a table showing model selections of enzymatic reactions that will enhance the amino acid production capabilities of E. coli.

FIG. 22 is a table showing evolution of minimal reaction sets under decreasing growth conditions.

FIG. 23 is a table showing metabolites uptaken or secreted at each target growth rate on an optimally engineered medium.

FIG. 26 is a table showing evolution of minimal reaction sets for a second set under decreasing growth requirements.

FIG. 27 is a table showing functional classification of minimal network reactions for growth on an optimally engineered medium.

FIG. 28 is a table showing a comparison of minimal metabolic gene/reaction sets based on functional classification.

DETAILED DESCRIPTION OF THE INVENTION

1. Overview

Figure 1:
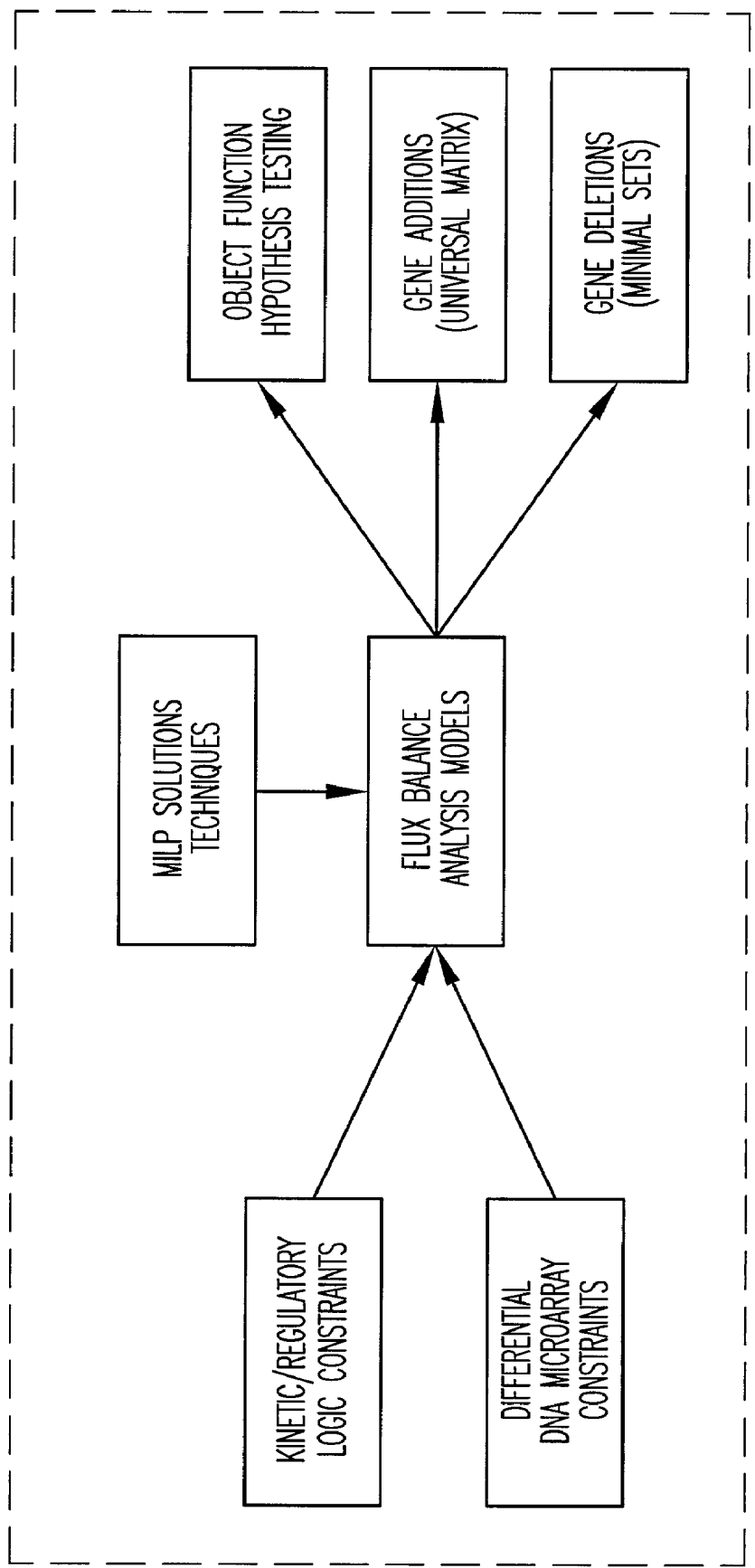
FIG. 1 is a block diagram showing an overview of the present invention.

FIG. 1 illustrates the framework of the present invention. This framework improves upon flux balance analysis (FBA) models through incorporation of particular constraints. These constraints incorporate, without limitation, qualitative kinetic information, qualitative regulatory information, and/or DNA microarray experimental data. Preferably, these constraints are logic constraints that can be represented with binary variables. The invention also provides for including computation procedures such as mixed-integer linear programming into the framework in order to use the model to arrive at a solution. As shown in FIG. 1, the model provides for determining metabolic performance/robustness in the face of gene additions or deletions. In addition the model provides for testing whether experimental flux data, under different substrates and carbon/oxygen uptake rates are consistent with different hypothesized objective functions.

The present invention involves a process for tightening the flux boundaries derived through flux balance models and subsequently probing the performance limits of metabolic networks in the presence of gene additions or deletions. Given the large number of genes (hundreds to thousands) available for recombination, present optimization formulations reach and sometimes exceed the limit of what can be solved with state of the art mixed-integer linear programming solvers. The present invention meets the dual objectives of constructing modeling formulations that enable an effective query of the performance limits of metabolic networks and provide customized techniques for solving the resulting mixed-integer linear programming problems.

2. Objective Function Hypothesis Testing

The present invention provides for an unbiased, mathematically rigorous framework for testing whether experimental flux data, under different substrates and carbon/oxygen uptake rates, are consistent with different hypothesized objective functions. A. Varma and B. O. Palsson, Bio/Technology 12, 994 (1994); R. A. Majewski and M. M. Domach, Biotechnol. Bioeng. 35, 732 (1990). Rather than starting by postulating such an objective function, or even accepting that there exists an objective function governing cellular behavior, the quantitative framework of the present invention is based on inverse optimization that enables researchers to test, disprove or fine tune the consistency of different hypotheses. Note that while one can never prove the existence of such an objective function, the framework is useful for rigorously testing whether experimental data is consistent or inconsistent with a postulated objective function and how this may change under different environmental conditions.

Figure 2A:
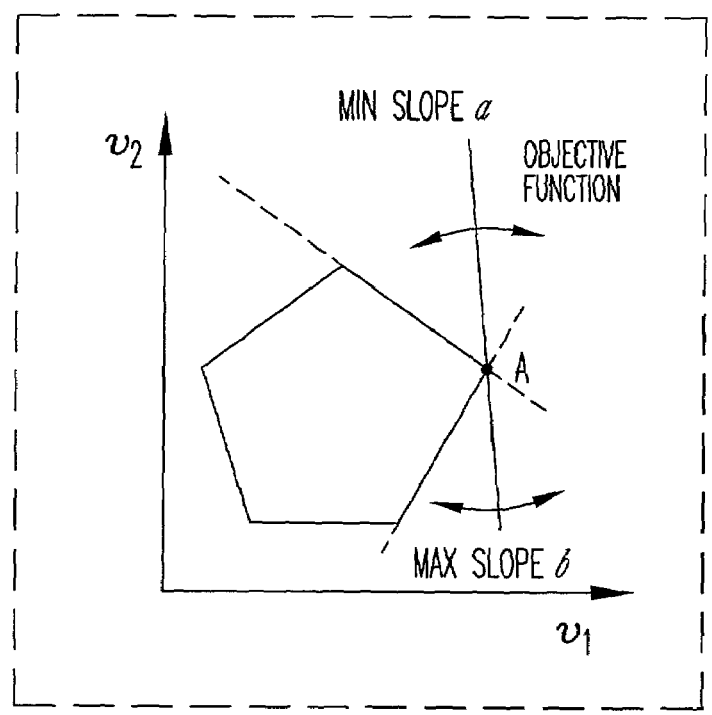
FIG. 2 is a diagram of multiple objective function slopes consistent with the same optimum point.

Inverse optimization concepts that were pioneered in geophysics for the identification of model parameters for systems reaching optimality given a set of observables are applied here. Specifically, the present invention provides for finding the coefficients $c_j$ in a hypothesized linear objective function $\Sigma_j c_j v_j$ that are consistent with the subset of observed fluxes $v^*_j$ (e.g., substrate/oxygen uptakes, growth rate, etc.). In general, not single but rather a range of values for the coefficients $c_j$ are consistent with a set of observed fluxes. This is illustrated with FIG. 2A in two dimensions.

Figure 2B:
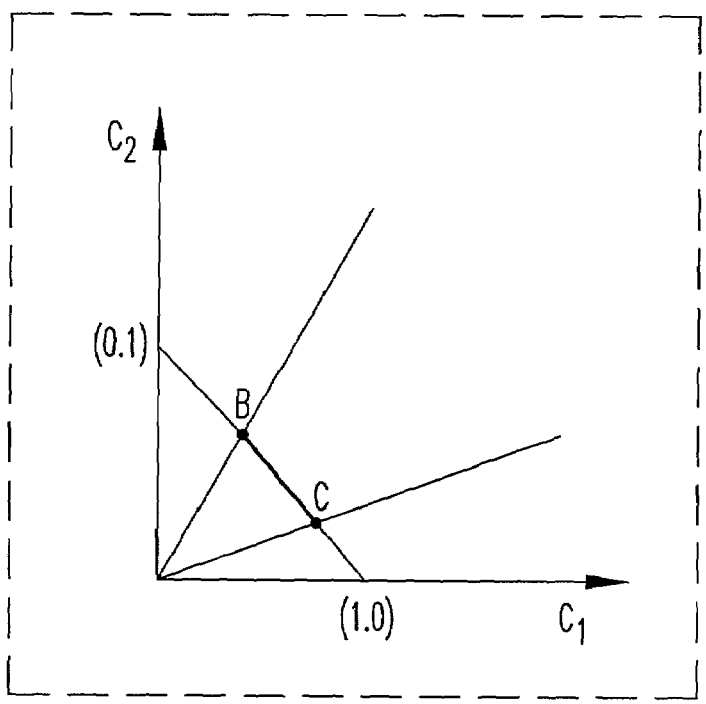

Any objective function $c_1 v_1 + c_2 v_2$ whose slope $(-c_2/c_1)$ is between values a and b is consistent with the optimality of point A. This gives rise to the range of values for $c_1$ and $c_2$ denoted by the line segment between points B and C shown in FIG. 2B that are consistent with the optimality of point A. Note that $c_1$ and $c_2$ were scaled so that $c_1 + c_2 = 1$. In the general n dimensional case, the set of $c_j$ values in compliance with an optimum $v^*_j$ forms a polytope.

The general problem is addressed using the ideas introduced by Ahuja and Orlin (2001). R. K. Ahuja, et al, *Network Flows, Theory Algorithms, and Applications,* Prentice Hall, Englewood Cliffs, N.J. 1993. Given an observed subset of fluxes $v^*_j$, the set of objective function coefficients $c_j$ can be determined by finding all multiple optimal solutions of the restricted dual feasibility problem solved in the space of dual variables $\alpha_i$ and the linear objective function coefficients $c_j$.

Figure 3A:
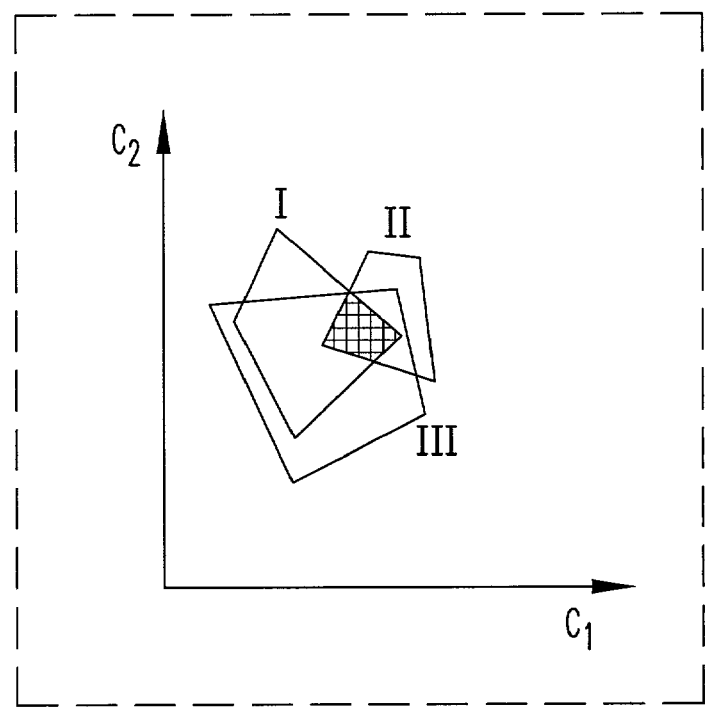
FIG. 3 is a set of feasible objectives for different conditions.
Figure 3B:
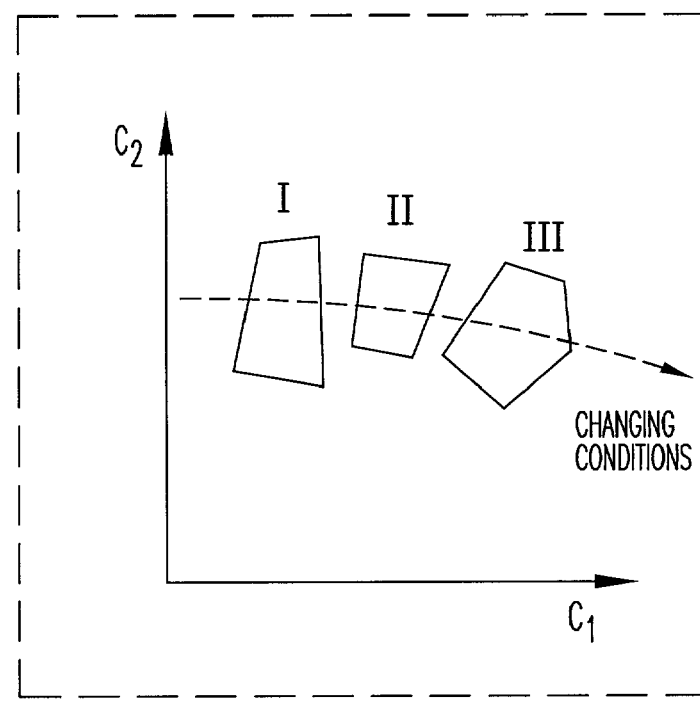

The dual variables $\alpha_i$ quantify the relative importance of a metabolite i towards improving the objective function. The solution of the restricted dual problem systematically characterizes the set of all possible $c_j$ values consistent with a subset of observed fluxes $v^*_j$. These alternate optimal solutions can be obtained as a byproduct of the simplex method since any basic feasible solution from the simplex tableau defines a vertex of the polytope formed in the $c_j$ space. An alternate method using integer cuts can also be employed. S. Lee, et al., Comput. Chem. Eng. 24, 711 (2000). The present invention contemplates that with these techniques a determination can be made as to whether the polytopes overlap considerably (see FIG. 3A) or migrate systematically (see FIG. 3B) as the as the substrate choice or uptake rate of carbon/oxygen changes. This set of quantitative tools provides an unbiased framework for researchers to test the range of validity (if any) of different hypotheses.

3. Kinetic/regulatory Logic Constraints

Flux balance models, by relying solely on stoichiometric balances and uptake rates, are guaranteed not to exclude any feasible flux distributions. However, this versatility may lead to overly optimistic expectations if the results are not interpreted properly. The flux distributions within the cell are ultimately uniquely determined by the regulatory mechanisms within the cell, the kinetic characteristics of cellular enzymes, and the expression of these enzymes. Assuming cells operate in a stoichiometrically optimal fashion may yield metabolic flux distributions not available to the cell. The present invention provides for multiple methods for tightening the predicted stoichiometric flux boundaries by FBA models. A first strategy involves attempting to ensure that flux changes identified through FBA are consistent, in a qualitative sense, with the kinetics and regulatory loops of the metabolic network. By uncovering unreachable domains within the stoichiometric flux boundaries the predictive capabilities are improved. A second strategy entails incorporating experimentally obtained data into the FBA model. The present invention includes a mathematically sound framework for superimposing DNA array differential expression data into FBA models.

3.1 Kinetic and Regulatory Loop Consistency

Figure 4:
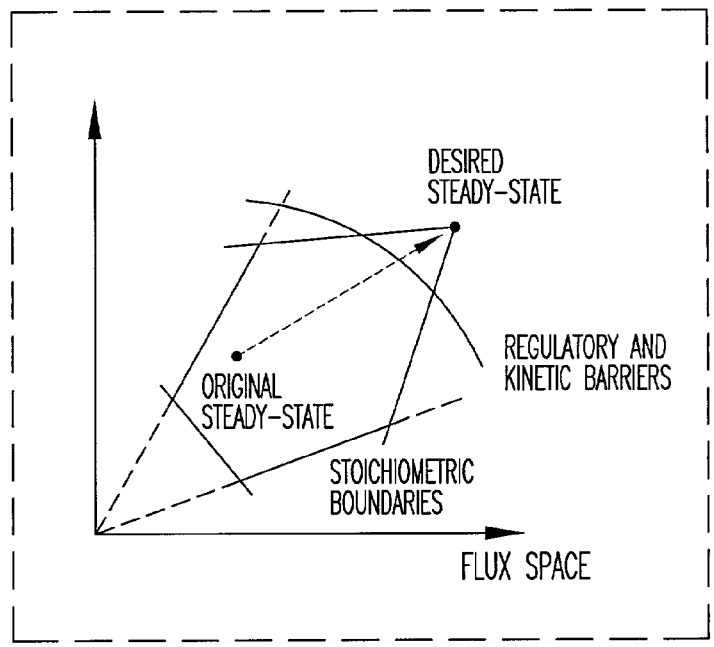
FIG. 4 is a pictorial representation of stoichiometric boundaries, kinetic/regulatory barriers and a new optimal steady state.

The key question addressed here is whether the optimal flux distributions predicted by the FBA models are reachable by the cell or whether kinetic and/or regulatory boundaries will prohibit the system from reaching the stoichiometric boundaries (see FIG. 4).

The key idea we propose to explore is to ensure, by using logic relations, that when, in response to environmental changes, the metabolic network shifts from one steady-state to another, up or down changes in metabolite concentrations are consistent with up or down changes in reaction fluxes.

Figure 5:
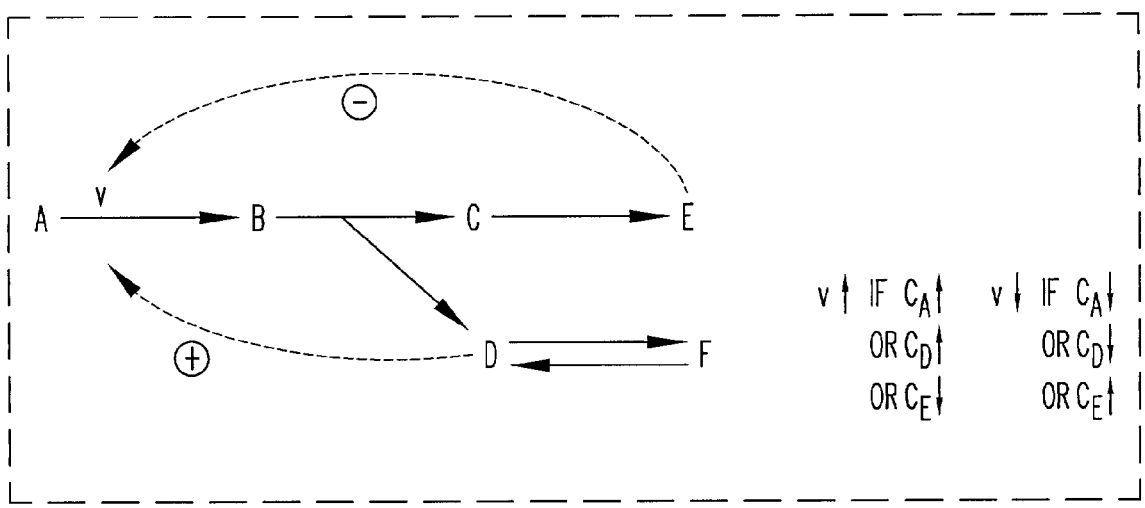
FIG. 5 is a diagram of a simple network showing the application of logic constraints.

Specifically (see FIG. 5), flux v can increase, in the absence of enzyme engineering, only if the concentration $C_A$ of reactant A or the concentration $C_D$ of activator D increase or the concentration $C_E$ of inhibitor E decreases. Clearly, changes in the reaction fluxes and metabolite concentrations are coupled and even in the absence of detailed quantitative kinetic/regulatory information binding relations can be derived based on the direction of these changes. One such set of relations is described in detail below.

Specifically, for any reaction flux $v_j$ to increase above an initial base case value $v^o_j$, either the concentration of a reactant must increase, or the concentration of an activator must increase, or the concentration of an inhibitor must decrease and vice versa. Incorporating these logic constraints into the FBA framework, requires first a regulation matrix F to be established describing the effect of metabolite i on reaction j.

$$F_{ij} = \begin{cases} 1 & \text{if metabolite } i \text{ activates reaction } j \\ -1 & \text{if metabolite } i \text{ inhibits reaction } j \\ 0 & \text{if metabolite } i \text{ has no effect on reaction } j \end{cases}$$

Such a regulation matrix can be constructed based on information from the EcoCyc and MetaCyc databases. P. D. Karp, et al., Nucleic Acids Res. 28, 55 (2000). Additional database resources exist also for non-*E. coli* reactions. M. Kanehisa and S. Goto, S., Nucleic Acids Res. 28, 29 (2000). Two sets of 0-1 variables $x_i$ and $z_j$ are introduced to track up or down movements in metabolite concentrations and reaction fluxes respectively.

$$x_i = \begin{cases} 1 & \text{if the concentration of metabolite } i \text{ rises} \\ 0 & \text{otherwise} \end{cases}$$

-continued $$z_j = \begin{cases} 1 & \text{if reaction flux } j \text{ increases above original steady-state value} \\ 0 & \text{otherwise} \end{cases}$$

By utilizing these 0-1 variables, we incorporate the following logic constraints into the FBA model for safeguarding against the violation of some of the kinetic and regulatory barriers.

$$-(1-z_j)v_j^{max} + v_j^o \leq v_j \leq v_j^o + v_j^{max} z_j \quad (1)$$

$$\sum_{i:S_{ij}<0} x_i + \sum_{i:F_{ij}=1} x_i + \sum_{i:F_{ij}=-1} (1-x_i) \geq z_j, \forall j \quad (2)$$

$$\sum_{iS_{ij}<0}(1-x_i) + \sum_{iF_{ij}=1} x_i(1-x_i) + \sum_{iF_{ij}=-1} x_i \geq 1-z_j, \forall j \quad (3)$$

Relation (1) ensures that $v_j > v_j^o$ when $z_j=1$ as well as $v_j < v_j^o$ when $z_j=0$. Constraint (2) ensures that the concentration of a reactant must increase, the concentration of an activitor must increase, or the concentration of an inhibitor must decrease for a reaction flux $v_j$ to increase above its initial base case value $v_j^o$. The last constraint (3) ensures that the concentration of a reactant must decrease, the concentration of an activator must decrease, or the concentration of an inhibitor must increase for a reaction flux $v_j$ to decrease below the initial base case value. Revisiting the example of FIG. 3 constraints (2) and (3) for flux v yield $$x_A + x_D + (1-x_E) \geq z_1, \text{ and } (1-x_A) + (1-x_D) + x_E \geq 1 - z_1$$

Preliminary work on the alanine overproduction pathway for growth on glucose identified kinetic and regulatory bottlenecks that were not detectable by simple FBA models.

Figure 6A:
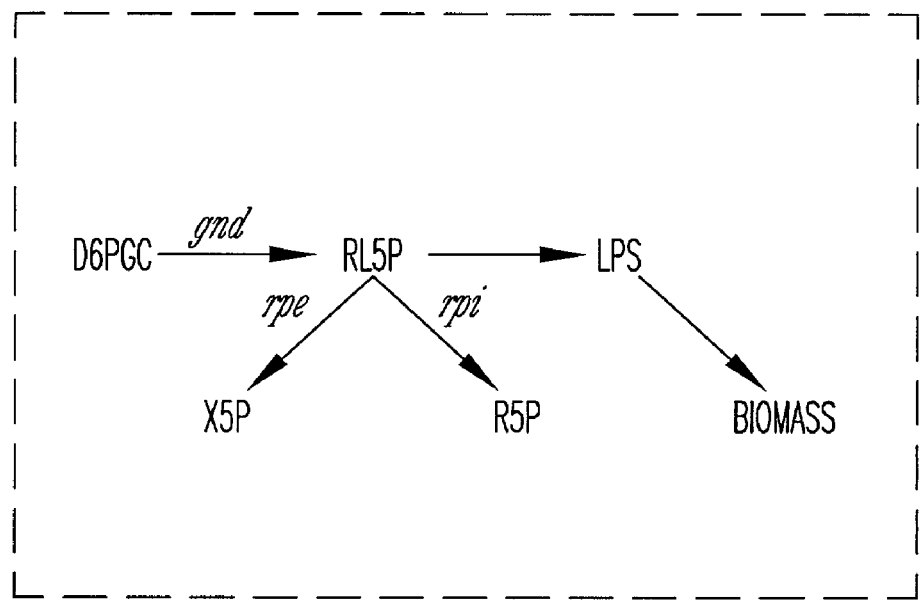
FIG. 6 is a diagram of two parts of a metabolic network where bottlenecks are identified.
Figure 6B:
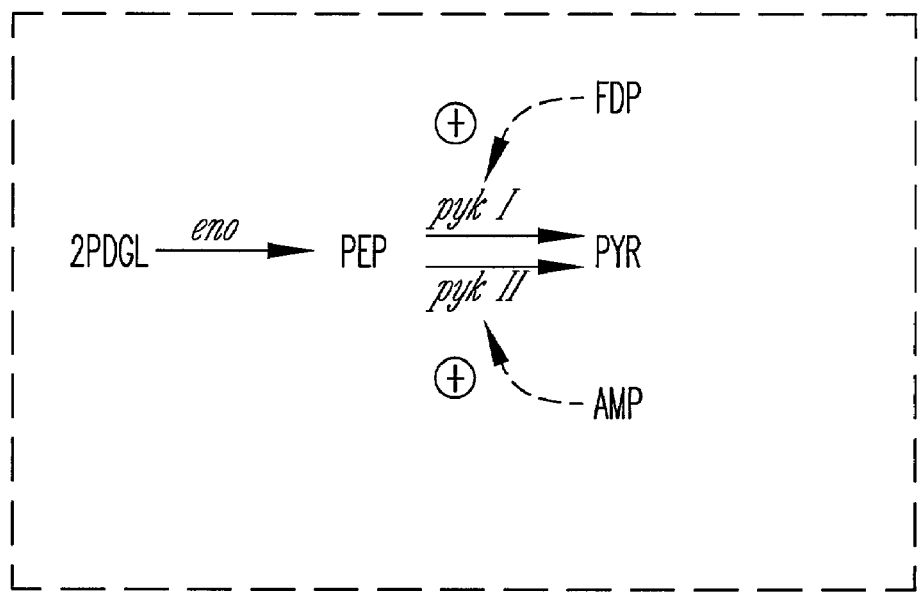

The first step in this analysis was to obtain the initial base case values for the reaction fluxes. These were obtained by solving the LP problem for maximum biomass formation. The second step was to solve a second LP problem constraining the biomass production to 80% of its optimal value and allowing for the overproduction of alanine. The third step involved resolving the second step scenario with the incorporation of the kinetic and regulatory logic constraints described above. This study revealed that the overproduction of alanine (2.688 mmol/10 mmol GLC) subject to regulation is about 20% less than the value predicted by the FBA model (3.298 mmol/10 mmol GLC) without the logic based regulatory constraints. More important than being able to identify this reduction is the capability to pinpoint specific flux bottlenecks. Analysis of the reaction fluxes revealed two potential bottlenecks limiting the performance of the network (see FIG. 6).

The first bottleneck (FIG. 6A) arises because in addition to the pentose phosphate pathway reactions, ribulose-5-phosphate (RL5P) is also a precursor to lyposaccharide (LPS) which is a component of biomass. Under less than optimal growth demands, the reaction flux from RL5P to biomass must decrease below its base case value. Thus the concentration of RL5P must decrease (only regulator). Therefore, the flux through ribulose phosphate 3-epimerase cannot increase above its base case value because the concentration of the reactant RL5P is decreasing. This diverts additional flux through the ribose-5-phosphate isomerase reaction. The second bottleneck (FIG. 6B) occurs because during alanine overproduction, more flux must pass through pyruvate kinase than under maximum growth conditions. In this study, at the base case, the FBA model chose pyruvate kinase II which is one of the two isoenzymes of pyruvate kinase. However, the flux through pyruvate kinase II cannot increase above its base case value because the concentration of both its activator (AMP) and its reactants are decreasing. The FBA model including regulation partially circumvented this barrier by increasing the flux through pyruvate kinase I since the concentration of an activator (FDP) of this reaction is increasing. This example suggests that the logic constraints, by capturing some kinetic and regulatory information, are capable of identifying at least some of the bottlenecks undetectable by simple FBA models without excluding any feasible flux distributions. Identifying these key fluxes as described above and then engineering the enzymes and regulation around them provides a straightforward debottlenecking strategy. The present invention contemplates that one skilled in the art and having the benefit of this disclosure can construct additional logic constraints in the spirit of the ones described above to further "tighten" the predictions of flux balance models.

4. Differential DNA Microarray Constraints

In addition to using qualitative kinetic and/or qualitative regulatory information to define logic constraints for enhancing the predictive capabilities of flux balance models, the present invention provides for defining constraints based on experimental differential DNA microarray data. The recent development of DNA microarray technology has started to revolutionize the investigation of cellular global regulation on the whole genome scale. DNA microarrays enable the determination of differential transcription profiles, consisting of the relative expression levels of individual genes under various experimental conditions. This allows one to infer which genes are up-regulated or down-regulated as an organism responds to external environmental changes. Already such studies have been initiated for *S. cerevisiae* (L. Wodicka, et al., Nat Biotechnol. 15(13), 1359 (1997)) and *E. coli*. C. S. Richmond, et al., Nucleic Acids Res. 27(19), 3821 (1999). The output of such experiments is typically a set of gene transcript levels normalized with respect to an original steady-state. For example, the differential transcript levels of 111 genes, involved in central metabolism and key biosyntheses, have been measured for an *E. coli* strain grown on either a glycerol or acetate medium relative to a glucose reference condition. M. K. Oh & J. C. Liao, Biotechnol. Prog. 16(2), 278 (2000). Thus, a transcript level of 1.5 for a gene in the *E. coli* strain grown on acetate indicates that this gene is up-regulated by 50% during growth on acetate as compared to growth on glucose. Although this methodology cannot detect any translational or post-translational genetic regulation, with a few exceptions, the transcriptional regulation is the main mode of regulation at least in *E. coli*.

The key challenge is that at present transcript levels cannot be used to infer quantitative changes in the corresponding flux levels. Instead, at best only a qualitative statistical correlation between changes in fluxes and transcript levels can be drawn. Based on a qualitative linking between fluxes and transcript levels, the present invention uses 0-1 variables to capture these trends. Let $T_j^i$ denote the normalized transcript level of gene coding for enzyme catalyzing reaction j upon the environmental change l. A value greater than one implies overexpression while a value less than one denotes underexpression. For the sake of simplicity of presentation, a one to one mapping of genes to reactions j≡k is assumed here. This can be easily relaxed if necessary. Consider binary variable $w_j$ defined as $$w_j = \begin{cases} 1, & \text{if the transcript and flux level changes are in the same direction} \\ 0, & \text{otherwise} \end{cases}$$

Given the definition of binary variables $w_j$, we can then write $$v_j^l \geq v_j^o - (1 - w_j^l)v_j^o, \text{ if } T_j^l > 1 \quad (4)$$

$$v_j^l \leq v_j^o + (1 - w_j^l)(v_j^{max} - v_j^o), \text{ if } T_j^l < 1 \quad (5)$$

where $v_j^o$ is the base flux level and $v_j^{max}$ a maximum allowable value. For $w_j=1$, these two constraints correctly enforce $v_j^l \geq v_j^o$ if $T_j^l > 1$ and $v_j^l \leq v_j^o$ if $T_j^l < 1$ respectively. For $w_j=0$ the two constraints yield obviously valid, non-binding constraints $v_j^l \geq 0$ and $v_j^l \leq v_j^{max}$ respectively. Perfect correlation between transcript and flux levels would have implied that all $w_j$ are equal to one. However, experimental studies have demonstrated that not 100% but rather on average about 80% of the genes exhibit transcript and flux levels changing in the same direction. Moreover, the further from unity the value of the transcript level is, the more likely it is for it to agree with the flux change direction. This motivates a probabilistic description for quantifying the likelihood that transcript changes translate to corresponding flux level changes in the same direction. Specifically, we will construct a statistical model of the form, $$P_j = 1 - \frac{1}{2}\exp\left[-\frac{(T_j - 1)}{T^{scale}}\right], \text{ for } T_j \geq 1,$$

$$P_j = 1 - \frac{1}{2}\exp\left[-\frac{(1/T_j - 1)}{T^{scale}}\right], \text{ for } T_j \leq 1$$

Figure 7:
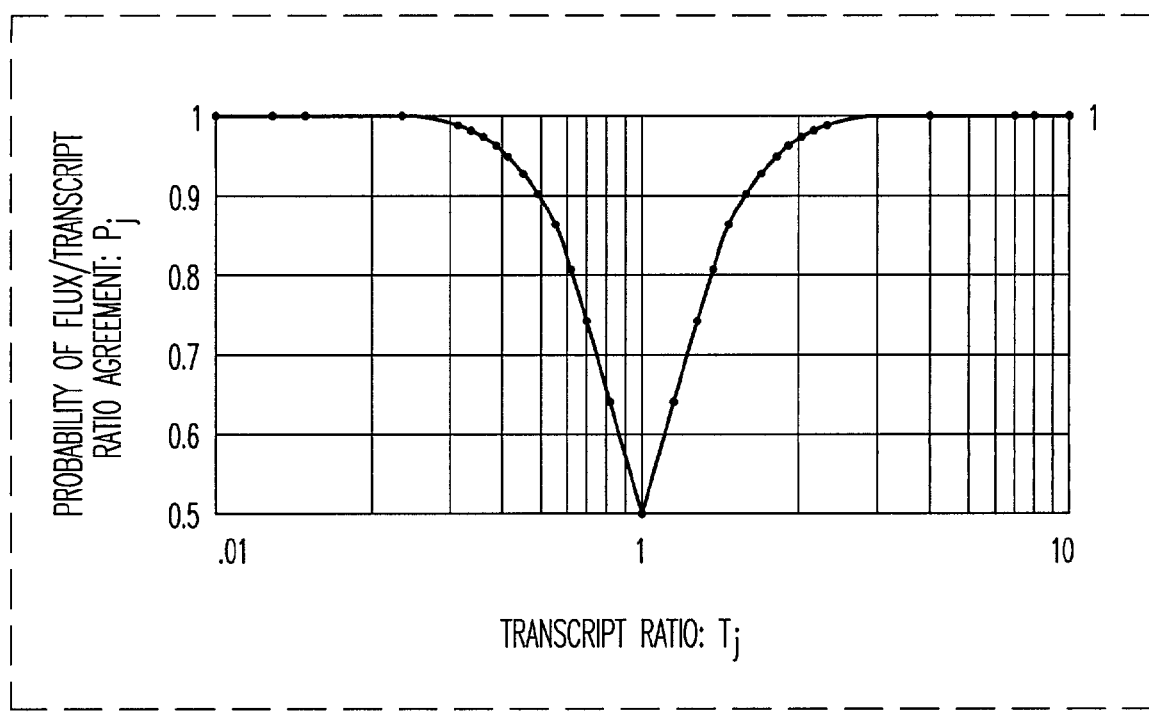
FIG. 7 is a logarithmic plot of probability of flux/transcript ratio agreement versus transcript ratio.

The scale $T^{scale}$ is chosen so as to control the range over which $P_j$ remains away from one. A value of 0.622 implies that 100% overexpression ($T_j=2$) or underexpression ($T_j=\frac{1}{2}$) confers a 90% probability of unidirectionality. FIG. 7 plots the probability $P_j$ of having unidirectional transcript and flux changes as a function of transcript level $T_j$. Note that for $T_j=1$, $P_j=0.5$ reflecting an equal chance for either outcome whereas when $T_j$ has very large positive or negative exponents $P_j$ approaches one. The present invention contemplates that more elaborate models for $P_j$ can be used, including those constructed by borrowing from mechanistic methods or other methods developed for linking transcript ratios to flux changes.

After using the $P_j$ probabilities to weigh the effect of each $w_j$ the following constraint is obtained:

$$\sum_j P_j w_j \bigg/ \left(\sum_j P_j\right) \geq \alpha \quad (6)$$

Here $\alpha$ is the fraction of genes j expected to have unidirectional transcript and flux changes. Thus, $\alpha$ quantifies the "agreeability" between the transcript ratios and the flux changes predicted by FBA. Augmenting FBA with constraints (4), (5) and (6) superimposes in a probabilistic sense the qualitative information encoded in the gene expression profiles of DNA microarray experiments. The above described probabilistic framework in two ways is employed in a number of different ways.

Figure 8:
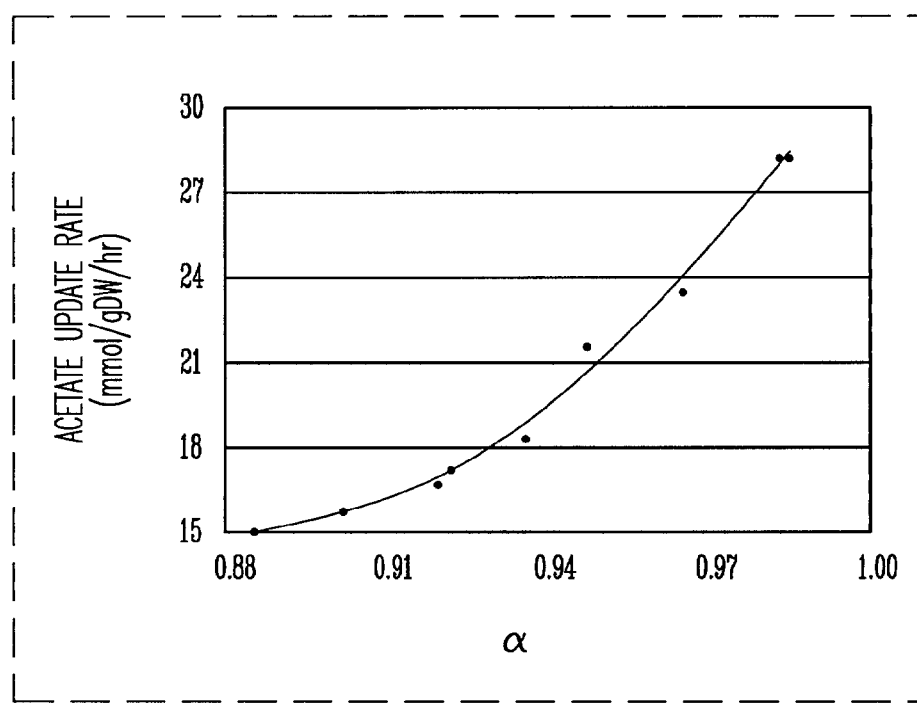
FIG. 8 is a plot of minimum acetate uptake rate versus α for a 0.3 hr$^{-1}$ growth rate.

The optimization of FBA models typically yields numerous alternate optima. An elegant algorithm has been proposed for identifying all of them by Lee et al., 2000. The DNA microarray data can be used to identify the subset of alternate optima that are consistent with the experimentally determined genetic expression levels. Specifically, the parameter $\alpha$ can be used to rank the multiple optima (Lee et al., 2000) typically obtained after the optimization of an objective function within an FBA model with respect to their agreeability with the DNA array data. Results with the data from Oh & Liao (2000) for the transition from growth on glucose to growth on acetate show that $\alpha$ can vary from 0.74 to 0.89 for the imposed growth rate of 0.3 hr$^{-1}$ depending on which alternate optimal solution is identified by the solver. Thus the FBA to expression profile agreeability can be improved as much as 20% by maximizing $\alpha$ for a given FBA optimal solution. The present invention also provides for the direct incorporation of the DNA microarray data into the FBA model. Here the sensitivity of the FBA objective to the imposed agreeability with the experimental transcript profiles can be adjusted by constraining the model to meet various values of $\alpha$. Results, shown in FIG. 8, for the same data from Oh & Liao (2000) show a quadratic trend between the minimum acetate uptake rate and the imposed agreeability parameter, $\alpha$.

5. Identifying Gene Candidates for Recombination

The explosive growth of annotated genes associated with metabolism calls for a systematic procedure for determining the most promising recombination choices. Until now, recombinant DNA technology has been used to add straightforward conversion pathways which introduce new and desirable cellular functions. Here the objective is to utilize flux balance analysis and mixed-integer programming tools to select the mathematically optimal genes for recombination into *E. coli* or other prokaryotes from a metabolic database encompassing many genes from multiple species. The resulting pathways need not lie directly on main production pathways, as they may enhance production indirectly by either redirecting metabolic fluxes into the production pathways or by increasing the energy efficiency of the present pathways.

A comprehensive stoichiometric matrix containing all known metabolic reactions from the Kyoto Encyclopedia of Genes and Genomes (KEGG) (Kanehisa and Goto, 2000) and Ecocyc (Karp et al., 2000), and other sources can be compiled and incorporated into the flux balance model of the model organism (e.g., *E. coli*). We refer to this multi-species stoichiometric matrix as the Universal stoichiometric matrix. This multi-species stoichiometric matrix is a valuable resource for exploring in silico gene recombination alternatives and examining which prokaryote will be the most advantageous choice for a given bioprocessing application.

Selecting up to h new genes to recombine into the host organism so that a metabolic objective v* is maximized can be formulated as an MILP problem. This is accomplished by augmenting the LP flux balance model with constraint $y_k=1$, $\forall k \in E$ that ensures that all *E. coli* genes are present as well as constraints $$\sum_{k \in NE} y_k \le h, 0 \le v_j \le v_j^{max}\left(\sum_k a_{jk} y_k\right)$$

that allow up to h foreign genes to be incorporated in *E. coli* out of the comprehensive list contained in the Universal matrix (i.e. NE). Here the host organism is assumed to be *E. coli* but in general any annotated prokaryotic microbe can be selected as the host organism. Reactions chosen by the model but absent in *E. coli* (i.e., all non-zero $y_k$ elements of NE) provide routes for manipulating the cellular metabolism through recombinant DNA technology.

Preliminary results using the flux balance *E. coli* model of Pramanik and Keasling demonstrate that improvements to seven amino acid production pathways of *E. coli* are theoretically attainable with the addition of genes from foreign organisms (see the table of FIG. 9). J. Pramanik and J. D. Keasling, Biotech. Bioeng. 56, 398 (1997).

Figure 10A:
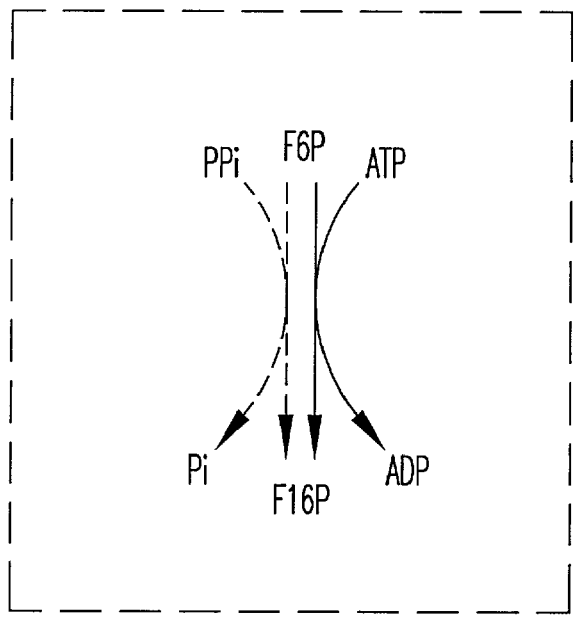
FIG. 10 is a diagram showing the pathway modifications introduced in a recombined network for growth on glucose.
Figure 10B:
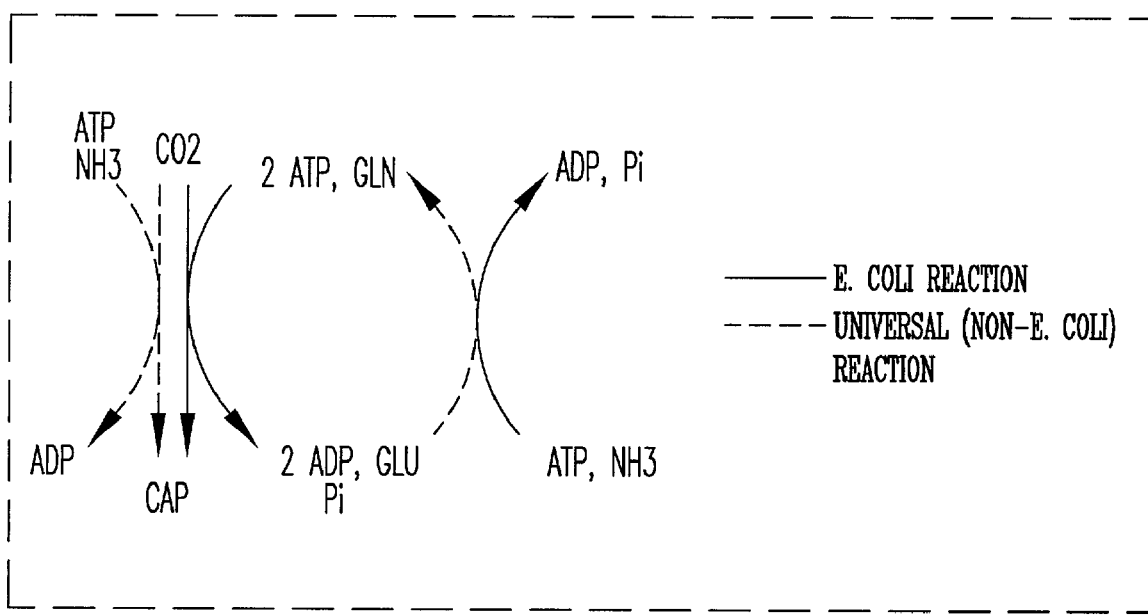

In most cases, only one or two genes were added to the original amino acid production pathway even though the complete list of 3,400 reactions was available for selection. The mechanism of all identified enhancements is either by: (i) improving the energy efficiency and/or (ii) increasing the carbon conversion efficiency of the production route. Manipulation of the arginine pathway showed the most promise with 8.75% and 9.05% improvements for growth on glucose and acetate, respectively. FIG. 10 shows the pathway modifications introduced in the recombined network for growth on glucose. Overall, the additional genes used by the Universal model save the original pathway three net ATP bonds increasing arginine production by 8.75%. Similar trends are revealed when other native and Universal amino acid production routes for glucose and acetate substrates are examined.

The models of the present invention that have been described can also be extended to encompass more gene candidates for recombination as they become available through ongoing genome projects. The present invention applies to any number of organisms, including other microorganisms of industrial significance. Even though *E. coli* is one of the most industrially significant microorganisms, other microbes confer advantages due to their relaxed regulatory mechanisms. For example, various species of the genera Corynebacterium and Brevibacterium have been employed to produce glutamate by exploiting a phospholipid-deficient cytoplasmic membrane enabling the secretion of glutamate into the medium. Riboflavin, or vitamin $B_2$, overproduces include *Eremothecium ashbyii* and *Ashbya gossypii* in which no repressive effects from ferrous ion are observed.

The logic based constraints of the present invention can be integrated with the gene selection MILP formulation to tighten the obtained predictions. By contrasting the optimal recombination changes identified for the production of different amino acids, recombination strategies that point towards simultaneous yield improvements of multiple amino acids are identified. The invention's optimization framework for guiding gene additions provides the quantitative means to study flux enhancements through foreign gene recombination from an ever-expanding database of available genes. Although complete gene-enzyme relationships are not currently known, the formulation allows the incorporation of this information as it becomes available.

6. Gene Deletions (Minimal Sets)

The recent explosion of fully sequenced genomes has brought significant attention to the question of how many genes are necessary for sustaining cellular life. A minimal genome is generally defined as the smallest set of genes that allows for replication and growth in a particular environment. Attempts to uncover this minimal gene set have included both experimental and theoretical approaches. Theoretical methods are based on the hypothesis that genes conserved across large evolutionary boundaries are vital to cellular survival. Based on this hypothesis, a minimal set of 256 genes was compiled by assuming that genes common to both *M. genitalium* and *Haemophilus influenzas* must be members of a minimal genome. A. R. Mushegian and E. V. Koonin, P. Natl. Acad. Sci. USA 93, 1026 (1996).

Interestingly, however, only 6 out of 26 *E. coli* open reading frames of unknown function conserved in *M. genitalium* were deemed essential to species survival. F. Arigoi, et al., Nat. Biotechnol. 16, 851 (1998). The existence of multiple, quite different, species and environment specific minimal genomes has long been speculated. M. Huynen, M., Trends Genet. 16, 116 (2000). The present invention provides for a computational procedure for testing this claim by estimating the minimum life-sustaining core of metabolic reactions required for given growth rates under different uptake conditions. This problem can be formulated as the following optimization problem $$\min \sum_{j=1}^{M} y_i \text{ subject to } \sum_{j=1}^{M} S_{ij} v_j = b_i, i = 1, \ldots, N \text{ with}$$

$$v_{biomass} \ge v_{biomass}^{target} \text{ and } 0 \le v_j \le v_j^{max} y_j$$

that solves for the smallest set of metabolic reactions that satisfies the stoichiometric constraints and meets a biomass target production rate $v_{biomass}^{target}$. Alternatively, instead of a biomass target, minimum levels of ATP production or lowest allowable levels of key components/metabolites could be incorporated in the model. One novel feature of this aspect of the invention is that whereas previous attempts utilized reductionist methodologies to extract the set of essential genes through a series of gene knock-outs, here we simultaneously assess the effect of all reactions on biomass production and select the minimal set that meets a given growth rate target (whole-system approach). A minimal gene set can then be inferred by mapping the enzyme(s) catalyzing these reactions to the corresponding coding genes.

Figure 11A:
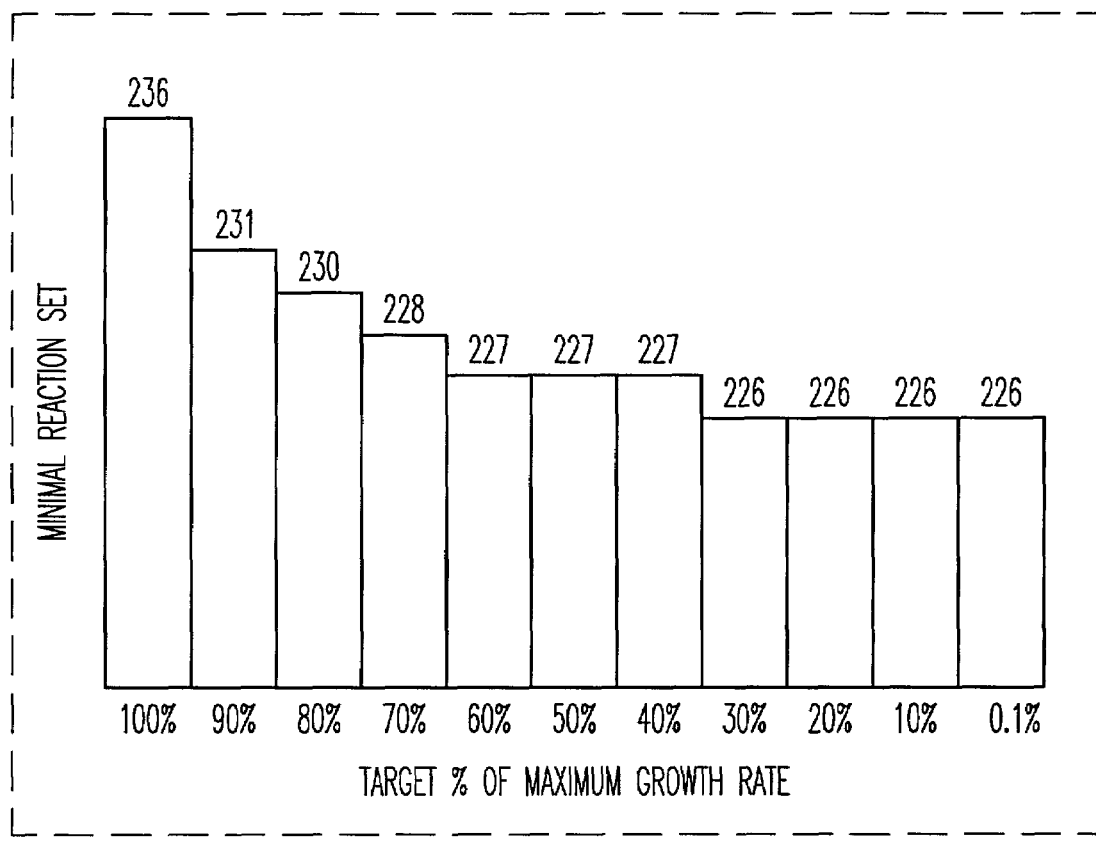
FIG. 11 is a graph showing the size of minimal reaction networks as a function of imposed growth rate for (a) growth on only glucose and (b) growth on a medium allowing for the uptake of any organic compound with a corresponding transport reaction.
Figure 11B:
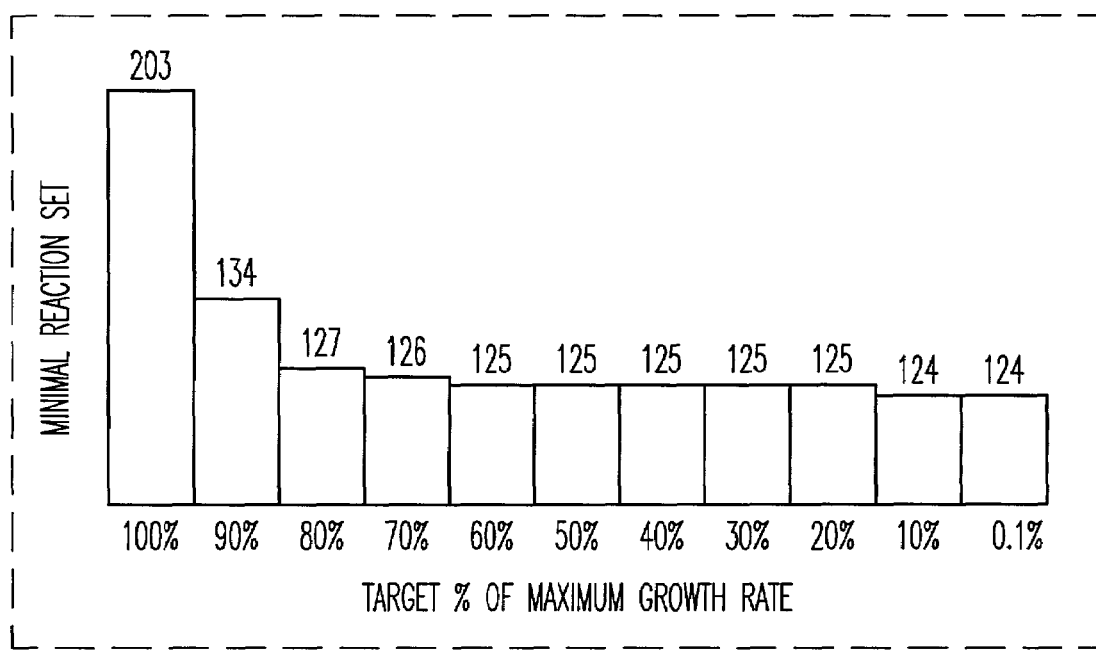

Results based on the *E. coli* FBA model of Edwards and Palsson for the first time quantitatively demonstrated that minimal reaction sets and thus corresponding minimal gene sets are strongly dependent on the uptake opportunities afforded by the growth medium and the imposed growth requirements. J. S. Edwards and B. O. Palsson, Proc. Natl. Acad. Sci. USA 97, 5528 (2000). Specifically, the minimal reaction network (subset of only *E. coli* reactions), was explored for different growth requirements under two contrasting uptake environments (a) restricting the uptake of organic material to glucose only and (b) allowing the uptake of any organic metabolite with a corresponding transport reaction. These two extreme uptake scenarios were chosen to model maximum and minimum reliance on internal metabolism for component synthesis and probe its effect on the minimum reaction set required. The minimum number of metabolic reactions as a function of the imposed biomass growth target, (as a % of the theoretically maximum), for the two uptake choices is shown in FIG. 11.

While it is predicted that an *E. coli* cell grown on a medium containing only glucose requires at least 226 metabolic reactions to support growth, a cell cultured on a rich optimally engineered medium could support growth with as few as 124 metabolic reactions. As expected, the minimal reaction set becomes larger by increasing the required growth rate. However, the magnitude of this increase is quite different for the two cases. In case (a) the minimal reaction set increases only from 226 to 236 to meet the maximum growth rate, however, in case (b) the minimal reaction set almost doubles going from 124 to 203. Furthermore, neither the minimal reaction sets nor their corresponding reaction fluxes were found to be unique. Even after excluding cycles and isoenzymes hundreds of multiple minimal sets were identified providing a computational confirmation of the astounding redundancy and flux redirection versatility of the *E. coli* network. More importantly for case (a), all minimal reactions sets identified included 11 out of 12 reactions whose corresponding gene deletions were determined experimentally to be lethal for growth on glucose. Earlier analyses (Edwards and Palsson, 2000) based on a single gene deletions conducted with this model using LP optimization were able to identify only 7 out of 12 lethal gene deletions motivating the importance of considering simultaneous gene deletions within an MILP framework.

The present invention contemplates that this framework can be built on by constructing different minimal reaction sets for not just *E. coli* but other species separated by wide evolutionary boundaries. By contrasting the obtained minimal sets, a comparison of minimal reaction sets (metabolic gene sets) along different evolutionary branches can be made. For example, organisms such as *M genitalium* and *H. influenza* can be used with results benchmarked against earlier studies (Mushegian and Koonin, 1996). By lumping reactions occurring in many different species within the Universal stoichiometric matrix described earlier a species independent minimal metabolic reaction set can also be constructed. The predicted *E. coli* based metabolic minimal set of 124 reactions/genes is comparable to the 94 metabolic genes included in the minimal gene set proposed by Mushegian and Koonin (1996). The present invention contemplates that this prediction gap can be reduced by (i) identifying more efficient reaction combinations, including those occurring in non-*E. coli* species, and (ii) by uncovering genes that are involved in the uptake or secretion of multiple (similar) metabolites reducing the total count. Clearly, the proposed computational framework is dependent upon a reaction-based analysis which inherently cannot account for genes associated with translation, replication, recombination, repair, transcription, cellular structure and genes of unknown function. However, it does afford the versatility to study different uptake/secretion environments as well as to encompass reaction sets from multiple species in the search for the metabolic minimal genome providing valuable insight and perspective to the questions of what is the minimal genome and how is it shaped by the environment. As more elaborate models are developed describing elementary functions of minimal cells, such as the work of Browning and Shuler for the initiation of DNA replication, more detail will be added to the modeling framework. S. T. Browning and M. L. Shuler, AICHE Annual Meeting, Session 69, Session 69, Los Angeles (2000).

Apart from developing a framework for rationally identifying "minimal" metabolic networks we also intend to exploit the capability of predicting in silico lethal gene deletions for different organisms and uptake environments. By identifying lethal gene deletions for pathogenic microbes as a function of the environment (e.g., *H. pylori*) a ranked list of promising targets for therapeutic intervention (i.e. interruption of gene expression) can be compiled. This list can further be refined by imposing constraints ensuring that human metabolism do not adversely be affected by repressing the expression of any of the pathogen genes included in the list.

7. Mixed-integer Linear Programming Solution Techniques

The modeling framework of the present invention further provides for computational procedures to be used to solve the network problems presented. The computational procedures to be used include mixed-integer linear programming techniques.

The algorithmic frameworks of the present invention in the context of gene addition, regulation, DNA array data superposition, genetic circuit elucidation and minimal reaction set identification inherently require the use of discrete optimization variables that give rise to MILP problems. Unlike LP problems which can be routinely solved even for hundreds of thousands of variables by employing commercial solvers (e.g., OSL, CPLEX, LINDO, etc.) with minimal or no user intervention, MILP problems are much more computationally challenging typically requiring not just more CPU time but also user intervention. Specifically, it is typically necessary to (i) cast the problem in a form that is more amenable to MILP solution techniques, and (ii) if the problem is still intractable for commercial solvers, to construct customized solution methodologies.

The key source of complexity in MILP problems in metabolic networks is the number of reactions/genes whose on or off switching as well as prediction of over- or under-expression requires binary 0-1 variables to describe. These problems belong to the class of generalized network problems (Ahuja et al, 1993) where each metabolite constitutes a node and each reaction represents an arc in the network. Given that existing FBA models for prokaryotes (Edwards and Palsson. 2000) contain hundreds of reactions and upcoming models for *S. cerevisiae* will likely be in the thousands motivates the need to harness complexity. In addition, the tremendous redundancy, redirection capability and multiplicity of steady-state solutions further exasperates complexity issues. In light of these challenges, some of the problems addressed by the present invention so far, particularly in the context of the minimal reaction sets required CPU's in the order of 50 hours.

A number of preprocessing and reformulation techniques can be used according to the present invention to alleviate the computational burden. These techniques include isoenzyme grouping, futile cycle exclusion and network connectivity constraints. Isoenzyme grouping refers to the aggregation of reactions differing only in the catalyzing enzyme (i.e., isoenzymes) in a single reaction. This reduces complexity by pruning the total number of binary variables. Futile cycle exclusion addresses the removal of sets of reactions (2 or more) which collectively recycle fluxes in a loop without any net effect on metabolism or energy generation. In general, a set K composed of K reactions forms a futile cycle if $$\sum_{j \in K} S_{ij} = 0, \forall i = 1, \ldots, N$$

The following constraint:

$$\sum_{j \in K} y_j \leq K - 1$$

inactivates at least one reaction breaking the cycle.

Connectivity constraints will ensure that if a reaction producing an intracellular metabolite is active, then at least one reaction consuming this metabolite must be active and vice versa. In addition, if a reaction transporting an extracellular metabolite into the cell is active, then at least one intracellular reaction consuming this metabolite must be active and vice versa.

State of the art commercial MILP solvers such as CPLEX6.1 and OSL which run on a multiprocessor unix platform IBM RS6000-270 workstation can be used to solve these types of problems. For problem sizes that are intractable with commercial MILP solvers, customized decomposition approaches can be used. For example, Lagrangean relaxation and/or decomposition by partitioning the original metabolic network into subnetworks loosely interconnected with only a handful of metabolites can be used. By iteratively solving many smaller problems instead of one large one computational savings are expected. Further, the present invention contemplates the use of disjunctive programming approaches which combine Boolean with continuous variables. These methods have been shown to be particularly effective for MILP problems where all the 0-1 (i.e., Boolean) variables are aggregated into logic constraints as is the case with many of the MILP formulations of the present invention.

8. EXAMPLE

Probing the Performance Limits of the *Escherichia coli* Metabolic Network Subject to go Gene Additions or Deletions The framework of the present invention can be applied to a number of metabolic network problems in a number of different contexts. The present invention has been used to probe the performance limits of the *E. coli* metabolic network subject to gene additions or deletions. According to this example, an optimization-based procedure for studying the response of metabolic networks after gene knockouts or additions is introduced and applied to a linear flux balance analysis (FBA) *E. coli* model. Both the gene addition problem of optimally selecting which foreign genes to recombine into *E. coli*, as well as the gene deletion problem of removing a given number of existing ones, are formulated as mixed-integer optimization problems using binary 0-1 variables. The developed modeling and optimization framework is tested by investigating the effect of gene deletions on biomass production and addressing the maximum theoretical production of the twenty amino acids for aerobic growth on glucose and acetate substrates. In the gene deletion study, the smallest gene set necessary to achieve maximum biomass production in *E. coli* is determined for aerobic growth on glucose. The subsequent gene knockout analysis indicates that biomass production decreases monotonically rendering the metabolic network incapable of growth after only 18 gene deletions.

In the gene addition study, the *E. coli* flux balance model is augmented with 3,400 non-*E. coli* reactions from the KEGG database to form a multi-species model. This model is referred to as the Universal model. This study reveals that the maximum theoretical production of six amino acids could be improved by the addition of only one or two genes to the native amino acid production pathway of *E. coli*, even though the model could choose from 3,400 foreign reaction candidates. Specifically, manipulation of the arginine production pathway showed the most promise with 8.75% and 9.05% predicted increases with the addition of genes for growth on glucose and acetate, respectively. The mechanism of all suggested enhancements is either by: (i) improving the energy efficiency and/or (ii) increasing the carbon conversion efficiency of the production route.

This example according to the framework of the present invention uses flux balance analysis and mixed-integer programming tools to select the mathematically optimal genes for recombination into *E. coli* from a metabolic database encompassing many genes from multiple species. The resulting pathways need not lie directly on main production pathways, as they may enhance production indirectly by either redirecting metabolic fluxes into the production pathways or by increasing the energy efficiency of the present pathways.

The recent upsurge of sequenced genomes has also brought significant attention to the question of which genes are crucial for supporting cellular life. Flux balance analysis modeling provides a useful tool to help elucidate this question. Although FBA models cannot simulate the regulatory structure alterations associated with gene deletions, these models can capture whether sufficient network connectivity exists to produce metabolites critical to cellular survival. In fact, a recent FBA model proposed by Edwards & Palsson (2000) was able to qualitatively predict the growth patterns of 86% of the mutant *E. coli* strains examined. This model was also used to identify some of the essential gene products of central metabolism for aerobic and anaerobic *E. coli* growth on glucose. J. S. Edwards and B. O. Palsson, BMC Bioinformatics 2000b 1, 1.

Determining the maximum number of tolerable gene deletions in a given metabolic system, however, requires a discrete optimization strategy in which multiple gene deletions can be simultaneously examined. A related approach utilizing discrete optimization to identify all alternate optima in linear metabolic models has been proposed by Lee et al. (2000).

According to the present invention, we examine how stoichiometric boundaries of cellular performance expand or contract in the presence of multiple gene additions or deletions. A FBA model of the cellular metabolism of *E. coli* is constructed incorporating the reaction pathways provided by Pramanik and Keasling (1997) along with modifications suggested by Karp (1999) based on more recent data. The modifications are either small molecule corrections based on more recent metabolic information or the removal of certain pathways now known to be absent from the *E. coli* genotype. A stoichiometric matrix as suggested by Schilling containing all metabolic reactions from the Kyoto Encyclopedia of Genes and Genomes is compiled and incorporated into the model. C. H. Schilling, et al., Biotech. Prog. 15, 288 (1999). We refer to this multi-species stoichiometric matrix as the Universal stoichiometric matrix. A short discussion of flux balance analysis will be presented next, followed by the gene addition and deletion formulations and their application to biomass and amino acid production in E. coli.

8.1 Flux Balance Analysis

Flux balance analysis (FBA) requires only the stoichiometry of biochemical pathways and cellular composition information to identify boundaries for the flux distributions available to the cell. Although microorganisms have evolved highly complex control structures which eventually collapse these available boundaries into single points, FBA models are still valuable in setting upper bounds for performance targets and in identifying "ideal" flux distributions. The underlying principle of FBA is mass balances on the metabolites of interest. For a metabolic network comprised of N metabolites and M metabolic reactions we have, $$\sum_{j=1}^{M} S_{ij} v_j = b_i, \forall i \quad (7)$$

where $S_{ij}$ is the stoichiometric coefficient of metabolite i in reaction j, $v_j$ represents the flux of reaction j, and $b_i$ quantifies the network's uptake (if negative) or secretion (if positive) of metabolite i. For all internal metabolites, $b_i$ is zero. Reversible reactions are defined simply as two irreversible reactions in opposite directions, constraining all fluxes to positive values.

Typically, the resulting flux balance system of equations is underdetermined as the number of reactions exceeds the number of metabolites and additional information is required to solve for the reaction fluxes. Several researchers have measured external fluxes to add as constraints to their underdetermined models, rendering them completely determined or over-determined. H. Jorgensen, et al., Biotechnol. Bioeng. 46 117 (1995); E. Papoutsakis and C. Meyer, Biotechnol. Bioeng. 27, 50 (1985); E. Papoutsakis and C. Meyer, Biotechnol. Bioeng. 27, 67 (1985); A. Pons, et al. Biotechnol. Bioeng. 51(2), 177 (1996). However, additional assumptions such as removing reaction pathways are often needed before external flux measurements can completely define a system, and neglecting potentially active pathways to render a system completely defined may cause large changes in calculated fluxes (Pramanik, 1997). A popular technique for investigating metabolic flux distributions is linear optimization (Varma, 1994). The key conjecture is that the cell is capable of spanning all flux combinations allowable by the stoichiometric constraints and thus achieving any flux distributions that maximize a given metabolic objective (e.g., biomass production). The linear programming model for maximizing biomass production is:

$$\text{Maximize} \quad Z = v_{biomass}$$
$$\sum_{j=1}^{M} S_{ij} v_j = b_i, \forall i$$
$$b_i \in \mathbb{R}, \forall i$$
$$v_j \in \mathbb{R}^+, \forall j$$

where $v_{biomass}$ is a flux drain comprised of all necessary components of biomass in their appropriate biological ratios. Other objective functions such as maximizing metabolite production, maximizing biomass production for a given metabolite production, and minimizing ATP production have also been investigated in the prior art.

8.2 Escherichia coli Stoichiometric Models

Microbial stoichiometric models incorporate collections of reactions known to occur in the studied species for simulating metabolism. The complete sequencing of the E. coli genome makes it a model organism for the study presented in this paper because extensive knowledge regarding its biochemical pathways is readily available. Varma and Palsson proposed the first detailed FBA E. coli model capable of predicting experimental observations. A. Varma and B. O. Palsson, J. Theor. Biol. 165, 503 (1993). The stoichiometric matrix included 95 reversible reactions utilizing 107 metabolites for simulating glucose catabolism and macromolecule biosynthesis. This model was used to investigate byproduct secretion of E. coli at increasingly anaerobic conditions and was able to predict the right sequence of byproduct secretion consistent with experimental findings: first acetate at slightly anaerobic conditions, then formate, and finally ethanol at highly anaerobic conditions. A. Varma, et al., Appl. Environ. Microb. 59, 2465 (1993). Building on the previous model, Pramanik and Keasling (1997) introduced a model that incorporated 126 reversible reactions (including 12 reversible transport reactions) and 174 irreversible reactions, as well as 289 metabolites. Pramanik and Keasling (1997) correlated the macromolecule composition of E. coli as a function of growth rate, and verified their model with experimental data. The model successfully predicted several levels of genetic control such as the glycoxylate shunt closing for growth on glucose and the PEP carboxykinase flux tending towards oxaloacetate. Furthermore, the glycoxylate shunt was active during growth on acetate while the flux through PEP carboxykinase was toward Phosphoenolpyruvate.

The stoichiometric E. coli model used in this study employs 178 irreversible, 111 reversible and 12 transport reactions compiled largely from the model published by Pramanik and Keasling (1997). The modifications to the Pramanik and Keasling stoichiometric matrix are given in the table of FIG. 12. They are primarily small molecule corrections (e.g., ATP in place of GTP for succinate thiokinase) or the removal of reactions now known to be absent from E. coli based on more recent data (Karp, 1999). Note that similar changes were also independently included in the most recently published E. coli model of Edwards and Palsson (2000). The metabolic network is fueled by transport reactions allowing an unconstrained supply of ammonia, hydrogen sulfate, and phosphate, along with a constrained supply of glucose or acetate to enter the system. Oxygen uptake is unconstrained to simulate aerobic conditions. Unconstrained secretion routes for lactate, formate, ethanol, glyceraldehyde, succinate, and carbon dioxide byproducts are provided by the transport reaction fluxes. The Universal model is constructed by incorporating 3400 cellular reactions from the Kyoto Encyclopedia of Genes and Genomes into the modified Keasling stoichiometric model. The Universal stoichiometric matrix contains all reactions known to occur in E. coli, as well as a number of reactions from other organisms.

8.3 Mathematical Modeling of Gene Deletions/Additions

Practically every metabolic reaction is regulated to some extent by one or more enzymes, produced by the translation of one or more genes. As a result, the removal of certain genes from microbial DNA sequences can be fatal or have little if any effect depending upon the role of the enzymes coded for by these genes. Conversely, the addition of certain genes through recombinant DNA technology can have either no effect or produce novel desirable cellular functionalities. Given a stoichiometric model of E. coli metabolism and the Universal stoichiometric matrix encompassing reactions occurring in multiple species, the goal of this section is to formulate a mathematical model that (i) captures cellular robustness in the presence of multiple gene deletions, and (ii) identifies additional genes from the Universal data set having the most profound effect on improving a given metabolic objective.

First, define K={k}={1, ..., M, ..., T} as the set of all possible genes where M represents the number of *E. coli* genes and T represents the total number of genes in the data set. This set can be partitioned into two subsets E and NE where subset E represents genes present in *E. coli* and subset NE represents genes present only in non-*E. coli* species:

$$E=\{k|1 \leq k \leq M\}$$

$$NE=\{k|M+1 \leq k \leq T\}$$

Subsequently, let binary variable $y_k$ describe the presence or absence of each gene k:

$$y_k = \begin{cases} 0 & \text{if gene } k \text{ is not expressed in host organism} \\ 1 & \text{if gene } k \text{ is present and functional} \end{cases}$$

The selection of the optimal gene choices for deletion or insertion from DNA recombination can be determined by appropriately constraining the number of non-zero elements in y. The case of removing a given number of genes, d, from *E. coli* can be investigated by including the following constraint:

$$\sum_{k \in \mathcal{E}} 1 - y_k \geq d$$

This ensures that no more than (M−d) genes are available to the metabolic network. Similarly, the effect of introducing any number of additional genes, h, can be investigated by utilizing:

$$y_k = 1 \forall k \in E \quad (8)$$

$$\sum_{k \in n\mathcal{E}} y_k \leq h \quad (9)$$

Equation (8) allows all *E. coli* genes to be present and functional if necessary, while equation (9) sets an upper limit to the number of allowable additions. The optimal genes selected by the model are obtained by determining which elements of NE are equal to one. In addition, since multiple genes often correspond to a single reaction and occasionally multiple reactions are catalyzed by an enzyme coded for by a single gene, the binary parameter $\alpha_{jk}$ is defined to describe which enzymes are coded for by which genes:

$$a_{jk} = \begin{cases} 0 & \text{if gene } k \text{ has no direct effect on reaction } j \\ 1 & \text{if gene } k \text{ codes for an enzyme catalyzing reaction } j \end{cases}$$

Parameter $\alpha_{jk}$ establishes links between genetic functional assignments and reactions. In order for a flux $v_j$ to take on a non-zero value, at least one gene must code for an enzyme catalyzing this reaction ($\alpha_{jk}=1$) and this gene must be present and functional in the host organism ($y_k=1$). Given that at least one gene must code for every enzyme we have, $$\sum_k a_{jk} y_k \begin{matrix} = 0 & \text{if no gene coding for the enzyme of reaction } j \text{ is functional} \\ \geq 1 & \text{if at least one gene coding for the enzyme of reaction } j \text{ is functional} \end{matrix}$$

This implies that the following constraint, $$L_j \left( \sum_k a_{jk} y_k \right) \leq v_j \leq U_j \left( \sum_k a_{jk} y_k \right)$$

ensures that $v_j=0$ if there exists no active gene k capable of supporting reaction j. In this case, $$\sum_k a_{jk} y_k = 0,$$

which in turn forces the value of $v_j$ to zero. Alternatively, if at least one such gene is functional, then $$\sum_k a_{jk} y_k \geq 1,$$

allowing $v_j$ to assume any value between a lower $L_j$ and an upper $U_j$ bound. These bounds are set by minimizing/maximizing respectively the given flux $v_j$ subject to the stoichiometric constraints. These problems are solved using CPLEX 6.6 accessed via the commercial software package GAMS. Problems with up to 3700 binary variables were solved on an IBM RS6000-270 workstation.

8.4 Gene Knockout Study

In this example according to the presentation, we determine what is the smallest gene set capable of maximizing biomass production on glucose substrate (uptake basis: 10 mmol) and what is the maximum number of gene deletions from this gene set that still maintains a specified level of biomass production. First, we maximized the biomass production flux, $v_{biomass}$. The solution yields the maximum theoretical level of biomass production ($v_{biomass}^{max}=1.25$ g biomass/gDW·hr) achievable by the metabolic network within the stoichiometric constraints. Next, the minimum number of genes that maintains a specified target level of biomass production $v_{biomass}^{target}$ (as a percentage of the maximum) is determined. The new objective function minimizes the total number of functional *E. coli* genes available to the cell subject to the constraint of setting biomass production $v_{biomass}$ greater than or equal to $v_{biomass}^{target}$. This problem is formulated as:

$$\text{Minimize } Z = \sum_{k \in \varepsilon} y_k$$

$$\text{subject to } \sum_{j=1}^{M} S_{ij} v_j = b_i, \forall i$$

$$L_j \left( \sum_k a_{jk} y_k \right) \leq v_j \leq U_j \left( \sum_k a_{jk} y_k \right)$$

$$v_{biomass} \geq v_{biomass}^{target}$$

$$v_j \in \Re^+, \forall j$$

$$b_i \in \Re, \forall i$$

$$y_k \in \{0, 1\}, \forall k \in E$$

where the nonzero elements of $y_k$ define the minimum gene set capable of attaining the target growth rate. The smallest gene set $M_{100\%}$, capable of sustaining the maximum theoretical growth rate is obtained by setting $v_{biomass}^{target} = 100\% \cdot v_{max}^{biomass}$. The model predicts that 202 non-transport intracellular reactions out of 400 available reactions (111×2 reversible reactions +178 irreversible reactions) are required to sustain $v_{biomass}^{max}$. These reactions include the glycolytic reactions, the pentose phosphate pathway, the TCA cycle, the respiratory reactions and all other anabolic and catabolic routes necessary for optimal growth.

Figure 13:
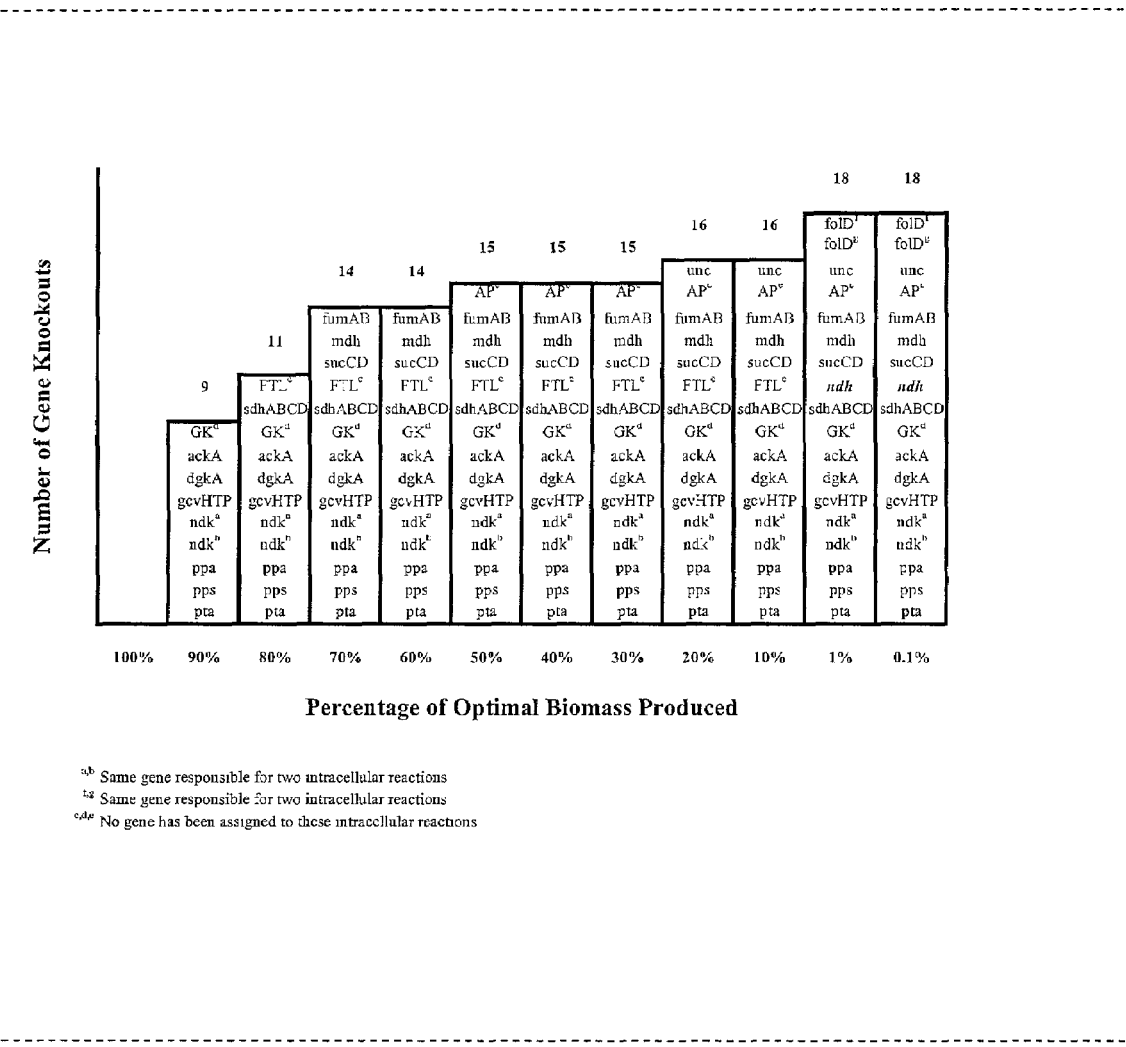
FIG. 13 is a graph showing gene knockouts at various biomass production levels for growth on glucose.

Given $M_{100\%}$, the next goal is to determine which of these genes could be knocked-out while still allowing the metabolic network to sustain specified sub-optimal growth rates. This is accomplished by setting $v_{biomass}^{target}$ equal to various percentages of $v_{biomass}^{max}$ and constraining the intracellular reaction fluxes outside of $M_{100\%}$ to zero. It must be noted that this assumption prevents the model from activating any genes outside of the $M_{100\%}$ set and the significance of this assumption will be discussed in the following section. The number of allowable gene knockouts for various biomass production levels are given in FIG. 13 while the selected gene removals are presented in the table of FIG. 14. As expected, as the biomass production demands on the network are lessened, the model tolerates more gene knockouts. However, the range of allowable knockouts is rather small. Specifically, the model tolerates at most 9 gene deletions with a biomass requirement of 90% $\cdot v_{biomass}^{max}$, while 18 gene removals render the network incapable of biomass formation. Thus the subset containing all elements of $M_{100\%}$ minus the 18 gene knockouts (194 genes) describes the smallest subset of $M_{100\%}$ capable of sustaining E. coli cellular growth for the employed FBA model. Additionally, it must be noted that all subsets include the seven experimentally verified essential gene products of central metabolism identified by the in silico gene deletion study of E. coli conducted by Edwards and Palsson (2000b).

8.5 Discussion on the Gene Deletion Study

Investigation of the specific gene knockouts provides interesting insight into the effect of various energy generation pathways. The suggested gene deletions imply that the energetic status of the network is improved as the required biomass production demands on the cell are reduced. This is demonstrated by the fact that as the biomass requirements are lessened, the optimization formulation sequentially eliminates pathways responsible for the formation of energy. One such observation involves the gradual degradation of the TCA cycle. When the model is constrained to produce only 80% of the optimal level of biomass, the network no longer utilizes the succinate dehydrogenase enzyme to produce $FADH_2$. Further reducing the biomass production requirement to 70% enables the removal of the fumAB, mdh, and sucCD genes forgoing the formation of one GTP and one NADH per unit reaction flux. The next major energy formation pathway to be eliminated occurs at a biomass production level of 20%. At this point, the energetic state of the cell is such that it no longer requires the formation of ATP from the cellular proton gradient. Finally, at the lowest biomass production levels, the cell no longer requires the oxidation of NADH to force protons across the cellular membrane.

This study provides insight into the dependence of cellular growth on various energy generation pathways and provides an estimate of the minimum number of metabolic genes capable of enabling cellular growth. The prediction of 194 genes is lower than the theoretical estimation of 256 by Mushegian and Koonin (1996) obtained by investigating the complete genomes of Haemophilus influenzae and Mycoplasma genitalium and assuming genes preserved across large phylogenetic distances are most likely essential. This was expected considering the inability of this reaction-based framework to account for genes associated with translation, transcription, replication, and repair, and the lumping of pathways by the stoichiometric model. A more practical comparison involves considering the number of metabolic genes included in the minimal gene set estimation. In this case, the predicted set of 194 metabolic genes overestimates the 94 metabolic genes included in the minimal gene set proposed by Mushegian and Koonin (1996). This overestimation arises in part because the effect of activating metabolic genes outside of the original optimal gene set was not investigated. This lowers the minimal gene set estimation by opening additional metabolic routes. Furthermore, this study only allowed glucose to enter the network as organic fuel and limited metabolic capacity can be compensated for by a proportionately greater dependence on the importation of nucleosides, amino acids, and other metabolites. C. A. Hutchison, et al., Science 286, 2165 (1999).

8.6 Amino Acid Production Optimization Studies

In this section, we identify mathematically optimal reaction pathways to recombine into the E. coli metabolic network to optimize amino acid formation for growth on glucose and acetate. We explored the theoretically optimal formation of all twenty amino acids. Each optimization run was performed for two cases: (i) including only the reactions present in E. coli, and (ii) allowing the model to select all reactions from the Universal stoichiometric matrix. The problem of maximizing the amino acid production is formulated by substituting amino acid accumulation, $b_{aa}$, in place of $v_{biomass}$ in equation (7), while the problem of maximizing the amino acid formation $b_{aa}^{UNV}$ of the Universal network is formulated as:

$$\text{Maximize } Z = b_{aa}^{UNV}$$

$$\text{subject to } \sum_{j=1}^{M} S_{ij} v_j = b_i, \forall i$$

$$y_k = 1, \forall k \in \varepsilon$$

$$L_j \left( \sum_k a_{jk} y_k \right) \leq v_j \leq U_j \left( \sum_k a_{jk} y_k \right)$$

-continued $$v_j \in \Re^+, \forall j$$

$$b_i \in \Re, \forall i$$

$$y_k \in \{0, 1\}, \forall k \in E \cup NE$$

Note that this formulation allows the selection of any number of reactions from the multi-species reaction list. Reactions chosen by the model but absent in *E. coli* (i.e., all non-zero $y_k$ elements of NE) provide routes for manipulating the cellular metabolism through recombinant DNA technology. The theoretical amino acid production capabilities of the *E. coli* metabolic network, with and without the additional reactions from the Universal matrix, are shown in the table of FIG. 9 for growth on glucose and acetate. It must be noted that it is the structural pathway changes predicted by the model that are more meaningful than the exact numerical values because these are theoretical maximum yield calculations. Predictions by the Varma and Palsson (1993) model are shown for comparison. As expected, the maximum production capabilities by the Varma and Palsson (1993) model are slightly below the predictions of the more complex employed model due to the additional metabolic routes available for production.

The results show that improvements to seven amino acid production pathways of *E. coli* are theoretically attainable with the addition of genes from various organisms. Manipulation of the arginine pathway shows the most promise, with 8.75% and 9.05% increases with additional genes for growth on glucose and acetate, respectively. The optimal recombinant asparagine pathway shows 5.77% and 5.45% increases over current *E. coli* growth on glucose and acetate, while cysteine production can be raised 3.57% and 3.80%, respectively. The histidine production pathway is revealed as another encouraging target for DNA recombination with 0.23% and 4.53% improvements available as well. The isoleucine, methionine, and tryptophan formation pathways offer the final three genetic objectives for enhancing production.

The enzymes responsible for introducing these various improvements to the *E. coli* amino acid production pathways are shown in the table of FIG. 15. In most cases, the addition of only one or two genes to the original amino acid production pathway results in an increased maximum theoretical yield even though the complete list of 3,400 reactions was available for selection. For example, introducing foreign genes coding for carbamate kinase and the pyrophosphate dependant version of 6-phosphofructokinase further optimizes arginine production for growth on glucose, while adding carbamate kinase and another gene coding for acetate kinase renders the arginine production pathway on acetate stoichiometrically optimal. Expressing the genes coding for aspartate-ammonia ligase and sulfate adenylyltransferase in *E. coli* results in the increased mentioned earlier in asparagine and cysteine productions, respectively. Only the production of isoleucine on glucose and acetate substrates and the production of methionine on acetate require over two additional enzymes to reach optimality according to the model.

8.7 Discussion on the Gene Addition Study

Figure 16:
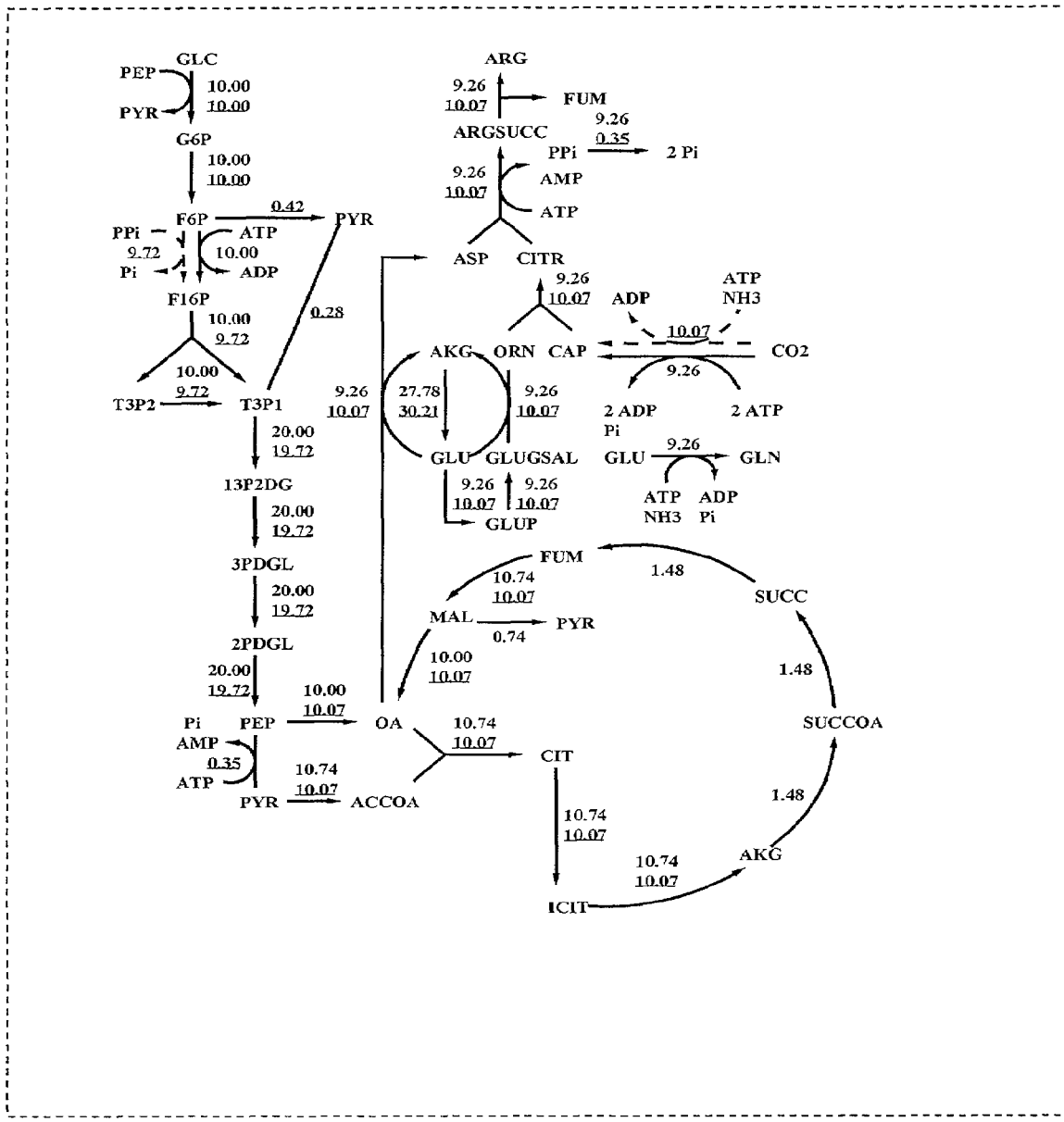
FIG. 16 illustrates optimal E. coli and Universal arginine production pathways for growth on glucose. The utilization of carbamate kinase and the pyrophosphate dependent analog of 6-phosphofructokinase by the Universal arginine production pathway preserves a net of 3 ATP phosphoanhydride bonds.

Careful examination of these amino acid pathways reveals how these additional enzymes improve the energetic efficiency of the original routes. The original and Universal arginine production pathways for growth on glucose are shown in FIG. 16. The two pathways differ in only two reactions—the pyrophosphate dependant analog of 6-phosphofructokinase in the Universal model replaces the ATP dependent version present in *E. coli*, and carbamate kinase in the Universal model replaces carbamoyl phosphate synthetase from the original *E. coli* model. The first improvement to energy utilization occurs because the Universal model 6-phosphofructokinase uses pyrophosphate formed from Argininosuccinate synthase reaction instead of ATP to transfer a phosphate group to fructose-6-phosphate in the third step in glycolysis. The *E. coli* model, which sends this pyrophosphate through pyrophosphatase for hydrolytic cleavage, in effect wastes the energy from this energy-rich phosphoanhydride bond. By recapturing this otherwise wasted energy, the pyrophosphate version of 6-phosphofructokinase requires one less ATP phosphoanhydride bond per arginine molecule produced.

Figure 17:
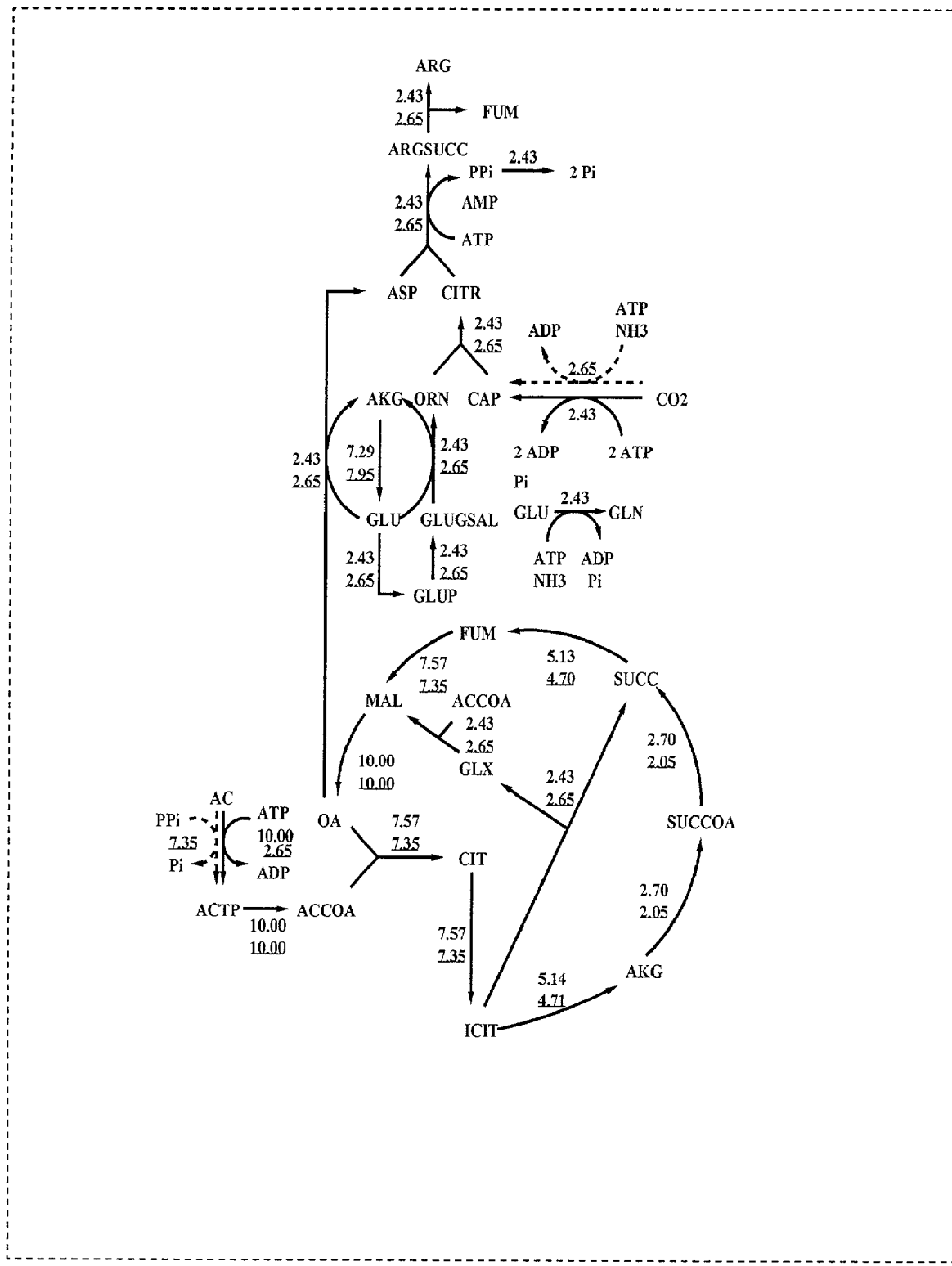
FIG. 17 illustrates optimal E. coli and Universal arginine production pathways for growth on acetate. The incorporation of carbamate kinase and the pyrophosphate dependent analog of acetate kinase by the Universal pathway saves 3 ATP phosphoanhydride bonds.

The second form of cellular energy savings is realized by the replacement of carbamoyl phosphate synthetase. The native carbamoyl phosphate synthetase creates one mole of carbamoyl phosphate from carbon dioxide at the expense of two ATP phosphoanhydride bonds. This reaction also requires an amino group of one glutamine molecule, which subsequently forms glutamate. Reforming glutamine from glutamate requires yet another ATP; thus each unit flux through carbamoyl phosphate synthetase requires three ATP. Carbamate kinase, incorporated in the Universal model, forms carbamoyl phosphate from carbon dioxide and ammonia at the expense of only one ATP. Therefore, carbamate kinase requires two less ATP bonds per unit flux of carbamoyl phosphate formed. Overall, the additional genes used by the Universal model save the original pathway three net ATP bonds increasing arginine production by 8.75%. A similar analysis can be performed on native and Universal arginine production routes from acetate substrate depicted in FIG. 17.

Figure 18:
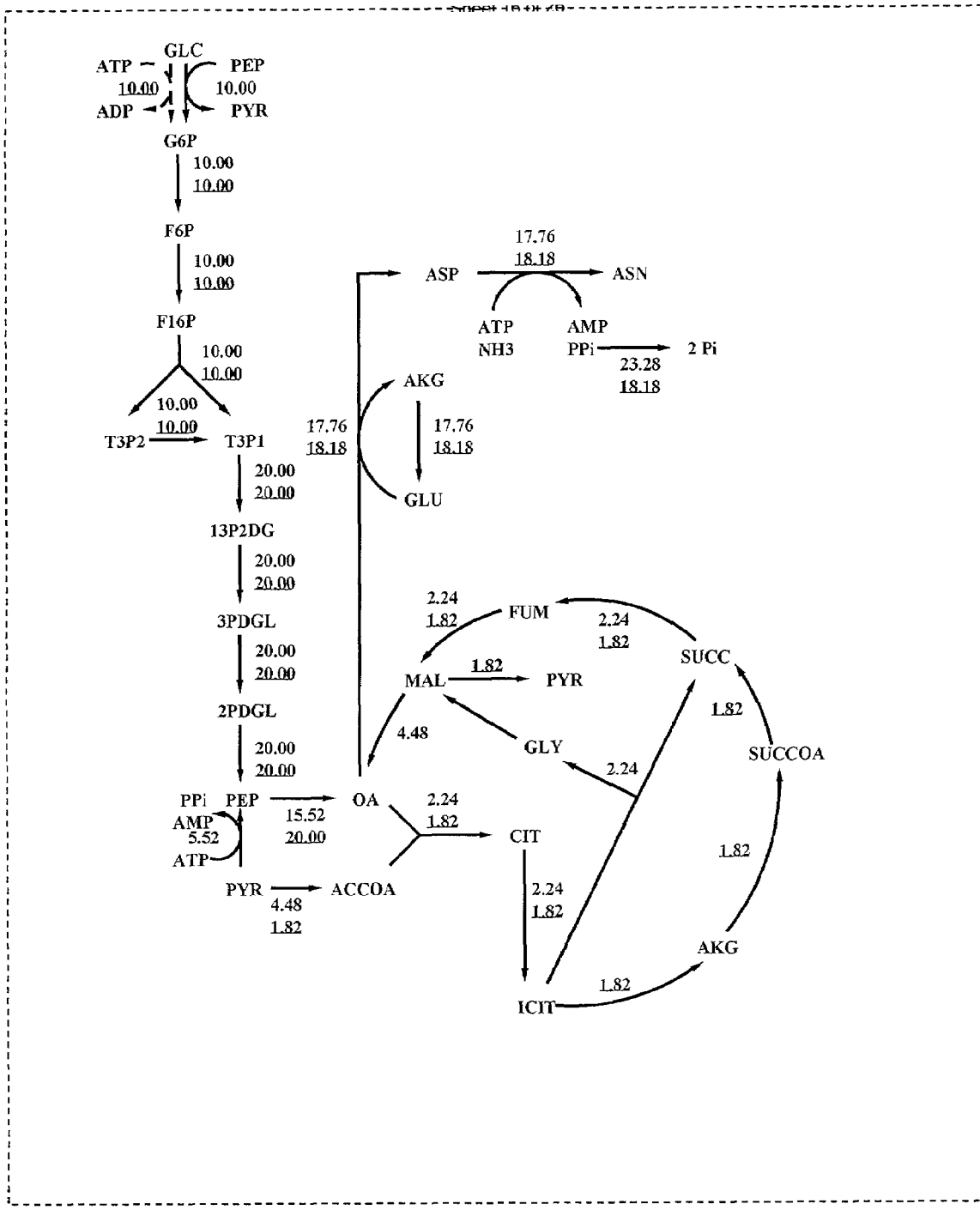
FIG. 18 illustrates optimal asparagine production pathways for two modes of glucose utilization: glucokinase and the phosphotransferase system.
Figure 19:
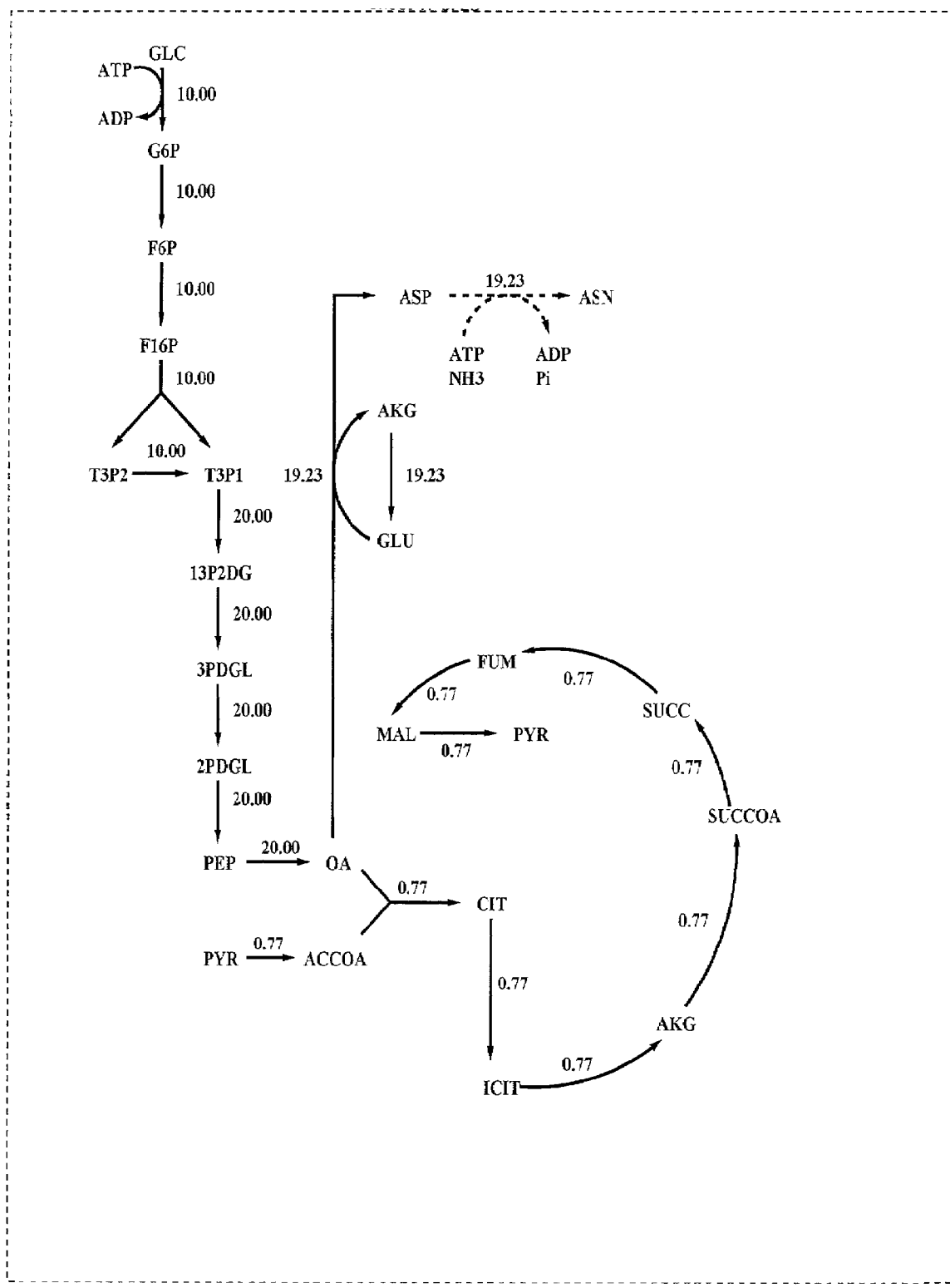
FIG. 19 illustrates an optimal Universal asparagine production pathway for growth on glucose. the Universal pathway conserves the equivalent of 1 ATP bond by using an ADP-forming aspartate-ammonia ligase instead of an AMP-forming version as shown in the previous figure.

The *E. coli* asparagine production pathway is shown in FIG. 18 for two modes of glucose entry into the metabolic network—glucokinase and the phosphotransferase system. Interestingly, the *E. coli* model prefers glucokinase to the more common phosphotransferase system for glucose entry during optimal asparagine production. Although glucokinase is known to play a minor role in glucose metabolism under normal conditions, replacement of the phosphotransferase system by this reaction increases asparginine production from 1.560 mol/mol glucose to 1.818 mol/mol glucose. Glucose entry via the phosphotransferase system requires substantial flux through phosphoenolpyruvate (PEP) synthase to regenerate PEP from pyruvate carrying the net expense of one ADP phosphoanhydride bond. Thus either over-expressing glucokinase in *E. coli* or adding a more active recombinant glucokinase enzyme may improve asparagine production. FIG. 19 illustrates the optimal Universal route for asparagine production on glucose. By choosing the ADP-forming aspartate-ammonia ligase enzyme over the AMP-forming version present in *E. coli*, the energy efficiency of this pathway is improved. Presently no pathways for the conservation of the pyrophosphate bond energy have been identified in *E. coli*, thus the formation of AMP uses the equivalent of two ATP phosphoanhydride bonds. In contrast, by forming ADP, the Universal pathway requires the breakage of only one phosphoanhydride bond per unit flux. In fact, the energy efficiency of the Universal model is such that the formation of asparagine does not require ATP formation from the trans-membrane proton gradient. This gradient is used solely to transport inorganic phosphate into the cell. This mechanism improves asparagine production 5.77% for growth on glucose and 5.45% for growth on acetate.

Figure 20:
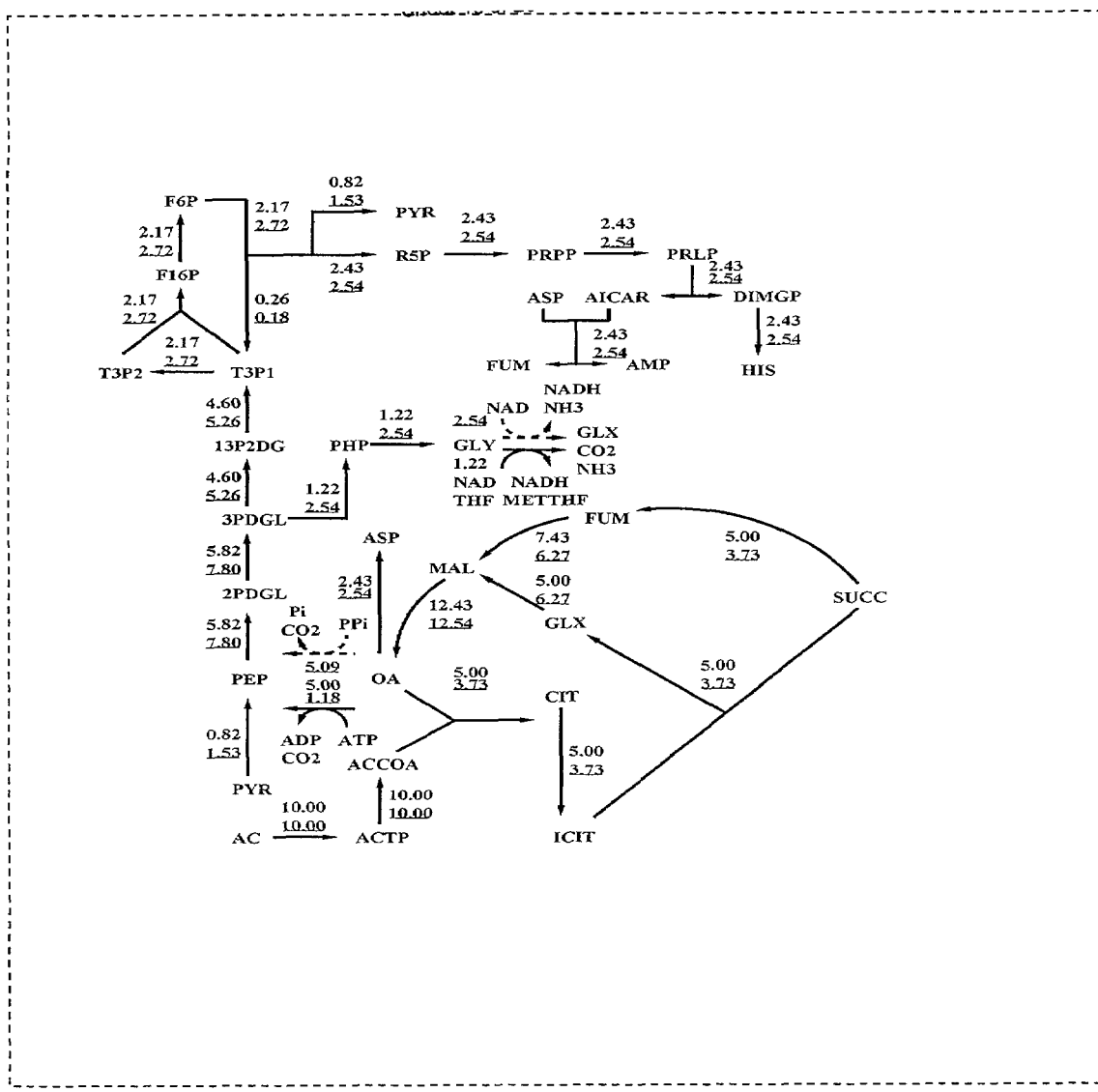
FIG. 20 illustrates optimal E. coli and Universal histidine production pathways for growth on acetate. Both the energy efficiency (2 ATP's) and carbon conversion efficiency of the Universal pathway are improved by the incorporation of a pyrophosphate dependent analog of PEP carboxykinase and glycine dehydrogenase, respectively.

The optimal histidine production pathways of the E. coli and Universal models for growth on acetate are shown in FIG. 20. Again, the Universal model selects a reaction to conserve the phosphoanhydride bond energy of pyrophosphate generated in this case by both ATP phosphoribosyltransferase and phosphoribosyl-ATP pyrophosphatase. Thus the Universal model is at least 2 ATP more efficient than the E. coli model per histidine molecule produced. In addition, the addition of glycine dehydrogenase to the E. coli model improves the carbon conversion of the native histidine pathway. Under optimal histidine production conditions in native E. coli, intracellular glycine is converted to carbon dioxide and ammonia by the glycine cleavage system. In this process, only one of glycine's carbons is conserved by its transfer to tetrahydrofolate. The Universal model, on the other hand, conserves both carbons by converting glycine to glyoxylate which subsequently is pumped back into the glyoxylate shunt. Both mechanisms improve the maximum theoretical yield of histidine 4.53%.

8.8 Conclusions

The proposed optimization framework provided the quantitative means to study metabolic network performance in response to gene deletions or additions. Metabolic network performance relates to either robustness in the face of gene deletions or flux enhancements through foreign gene recombination from an ever-expanding database of available genes. Although complete gene-enzyme relationships are not currently available, the formulation enables the incorporation of this information as it becomes available. The gene knockout analysis revealed that the E. coli metabolic network optimized for growth could endure an increasing amount of gene knockouts as its growth demands are lowered. Furthermore, the network could theoretically tolerate at most 18 gene deletions before biomass production is no longer possible. The gene addition studies revealed that adding additional options to the E. coli genotype by DNA recombination provided improvements to the maximum theoretical productions of seven amino acids. These improvements occur by one of two mechanisms: (i) by improving the energy efficiency or (ii) by increasing the carbon conversion efficiency of the production route.

The reliance of flux balance analysis strictly on stoichiometric characteristics is its greatest strength but also can be its most prominent weakness. The flux distributions within the cell are ultimately uniquely determined by the regulatory mechanisms within the cell, the kinetic characteristics of cellular enzymes, and the expression of these enzymes. Assuming cells operate in a stoichiometrically optimal fashion yields a wider boundary of metabolic flux distributions than may be available to the cell. Currently we are incorporating regulatory information into flux balance models with the use of logic constraints. These constraints will ensure that up or down movements in metabolite concentrations are consistent with up or down shifts in reaction flux values. A more tightly constrained model will give additional insight on how overproducing cellular products affects overall metabolic regulation. As the accuracy of metabolic models improves and the amount of information available for flux balance analysis grows, the framework introduced in this paper can be used to select the most optimal gene addition and/or deletion metabolic manipulations to perform.

9. EXAMPLE

Minimal Reaction Sets for *Escherichia coli* Metabolism Under Different Growth Requirements and Uptake Environments The framework of the present invention can be applied to a number of metabolic network problems in a number of different contexts. The framework of the present invention has also been applied to determining minimal reaction sets for E. coli metabolism under different growth requirements and uptake environments. According to the present invention, a computational procedure for identifying the minimal set of metabolic reactions capable of supporting various growth rates on different substrates is introduced and applied to a flux balance model of the E. coli metabolic network. This task is posed mathematically as a generalized network optimization problem. The minimal reaction sets capable of supporting specified growth rates are determined for—two different uptake conditions (i) limiting the uptake of organic material to a single organic component (e.g., glucose or acetate) and (ii) allowing the importation of any metabolite with available cellular transport reactions. We find that minimal reaction network sets are highly dependent on the uptake environment and the growth requirements imposed on the network. Specifically, we predict that the E. coli network, as described by the flux balance model, requires 224 metabolic reactions to support growth on a glucose-only medium and 229 for an acetate-only medium, while only 122 reactions enable growth on a specially engineered growth medium.

The recent explosion of fully sequenced genomes has brought significant attention to the question of how many genes are necessary for sustaining cellular life. A minimal genome is generally defined as the smallest set of genes that allows for replication and growth in a particular environment. Attempts to uncover this minimal gene set include both experimental and theoretical approaches. Global transposon mutagenesis was used by Hutchison et al. (1999) to determine that 265 to 350 of the 480 protein-coding genes of *Mycoplasma genitalium*, the smallest known cellular genome (580 kb), are essential for survival under laboratory growth conditions. Additional experimental work revealed that only 12% and 9% respectively of the yeast and *Bacillus subtilis* genomes are essential for cellular growth and replication. M. G. Goebl and T. D. Petes, Cell 46, 983 (1986); M. Itaya, FEBS Lett. 362, 257 (1995). Theoretical methods stem from the assumption that genes conserved across large evolutionary boundaries are vital to cellular survival. Based on this hypothesis, a minimal set of 256 genes was compiled by Mushegian and Koonin (1996) by assuming genes common to *M. genitalium* and *Haemophilus influenzae* must be members of a minimal genome. Interestingly, only 6 out of 26 E. coli open reading frames of unknown function conserved in *M. genitalium* were deemed essential to species survival (Arigoi, et al. 1998). The existence of multiple, quite different, species and environment specific minimal genomes has long been speculated (Huynen 2000).

Here we describe a computational procedure for testing this claim by estimating the minimum required growth-sustaining core of metabolic reactions under different uptake conditions. The latest stoichiometric model of *E. coli* metabolism proposed by Palsson and coworkers (Edwards & Palsson 2000b) is employed to identify the smallest set of enzymatic reactions capable of supporting given targets on the growth rate for either a glucose, an acetate, or a complex substrate. This flux balance analysis (FBA) model incorporates 454 metabolites and 720 reactions including the glycolysis, tricarboxylic acid (TCA) cycle, pentose phosphate pathway (PPP), and respiration pathways along with synthesis routes for the amino acids, nucleotides, and lipids. Growth is quantified by adding an additional reaction to the model simulating a drain on the various components of *E. coli* biomass in their appropriate biological ratios. F. C. Neidhardt, *Escherichia coli* and *Salmonella: Cellular and Molecular Biology*, ASM Press ed. Washington, D.C., 1996. By associating a gene to each metabolic reaction in the network, gene activations and inactivations are incorporated into the FBA model using logic 0-1 binary variables. The problem of minimizing the number of active metabolic reactions required to meet specific metabolic objectives (i.e., growth rates) is shown to assume the mathematical structure of a generalized network flow problem where nodes denote metabolites and connecting arcs represent reactions. Alternatively, instead of a biomass target, minimum levels of ATP production or lowest allowable levels of key components/metabolites could readily be incorporated in the model. A mixed-integer linear programming (MILP) solver, CPLEX 6.5 accessed via GAMS, is employed to solve the resulting large-scale combinatorial problems with CPU times ranging from minutes to days.

Based on the *E. coli* model, the minimal reaction network is explored for different growth requirements under two contrasting uptake environments (i) restricting the uptake of organic material to a single organic component and (ii) allowing the uptake of any organic metabolite with a corresponding transport reaction. These two extreme uptake scenarios were chosen to model maximum and minimum reliance on internal metabolism for component synthesis respectively, and probe their effect on the minimum reaction set required. Previous attempts utilized reductionist methodologies to extract the set of essential genes through a series of gene knockouts. Here we use an efficient computational procedure for selecting the minimal set by simultaneously considering the effect of all reactions on cell growth. A minimal gene set is then be inferred by mapping the enzyme(s) catalyzing these reactions to the corresponding coding genes. While the obtained results are, in principle, dependent on the specifics of the employed flux balance *E. coli* model (Edwards & Palsson 2000), they still provide valuable insight and perspective to the questions of what is the minimal genome and how is it shaped by the environment.

9.1 Results

The first case study involves identifying the minimal reaction set supporting *E. coli* growth on a glucose substrate. A detailed description of the employed modeling procedure is provided in the appendix. A constrained amount of glucose (<10 mmol/gDW·hr), along with unconstrained uptake routes for inorganic phosphate, oxygen, sulfate, and ammonia are enabled to fuel the metabolic network. Secretion routes for every metabolite capable of exiting the cell are also provided. Under these conditions, the FBA model predicts that the *E. coli* reaction network is capable of achieving a maximum theoretical growth rate of 0.966 g biomass/gDW·hr, which we will refer to as the maximum growth rate (MGR). By requiring the reaction network to match the MGR we determined that at least 234 reactions out of 720 are required for maximum growth on glucose.

The growth demands are then relaxed in subsequent studies to identify the minimal number of metabolic reactions required to meet various sub-maximal growth demands (% of MGR). Interestingly, the number of necessary metabolic reactions decreases only mildly with the falling growth demands imposed on the network as indicated by FIG. 21.

While a reaction set comprised of 234 reactions is needed for maximum growth, the minimal reaction set corresponding to growth rates of 30% and lower involves only 224 reactions. The same minimal reaction set persists even for growth rates as low as 0.1% of the MGR. In general, the reaction set reductions are attained by successively eliminating energy producing reactions occurring in (i) glycolysis, (ii) the TCA cycle, and (iii) the pentose phosphate pathway as the growth demands are lessened. However, certain reactions absent at higher growth rates enter the minimal sets at lower growth rates suggesting a much more complex mechanism of flux redirection than successive reaction elimination. A detailed description of the reactions entering/leaving the minimal reaction set as the imposed growth requirements are lowered is provided in the table of FIG. 22.

Figure 21:
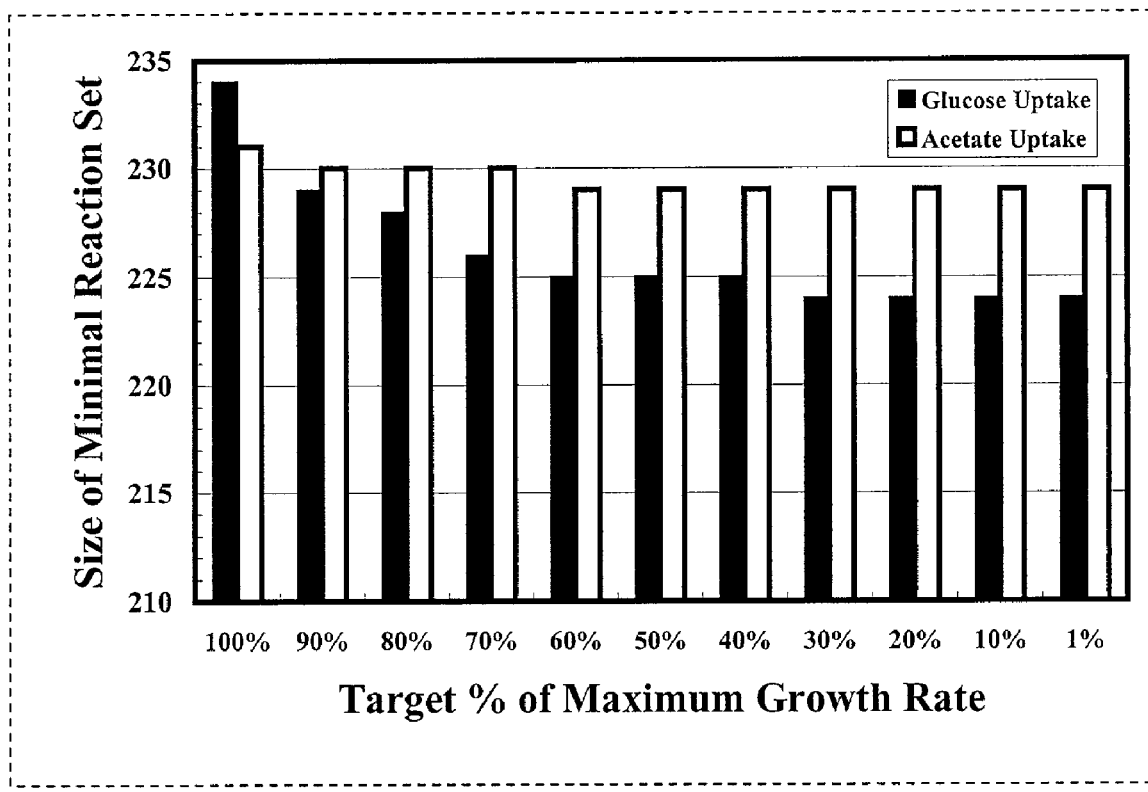
FIG. 21 is a graph of a number of reactions in each minimal set as a function of the imposed growth demands for a glucose or acetate-only uptake environment.

For comparison, a similar study enabling a constrained amount of acetate (<30 mmol/gDW·hr) to enter the network instead of glucose was performed (see FIG. 21). Here the network is much less tolerant of reaction set reductions than in glucose study. While for a glucose substrate the minimal network sizes decrease from 234 to 224 reactions as the growth demands are lowered, for an acetate substrate the network sizes reduce only from 231 to 229 reactions. This implies that the minimal reaction set size is not only dependent on the imposed biomass production requirements, but also on the specific choice for the single substrate.

It is important to note that neither the minimal reaction sets nor their corresponding reaction fluxes are unique. For example, for the 30% glucose uptake case we identified over 100 different minimal reaction sets containing exactly 224 enzymatic reactions without even counting the multiplicities associated with the 171 isoenzymes present in the network. Among most of these multiple minimal reaction sets, the activity and flux directions of the major pathways differ very little. Most variations are concentrated on the catabolic parts of the networks. For instance, while some minimal reaction sets secrete carbon dioxide, acetate, and fumarate as the only metabolic byproducts, other sets may also secrete varying amounts of formate, glycerol, and the amino acids phenylalanine and tyrosine. These results provide a computational confirmation of the astounding redundancy and flux redirection versatility of the *E. coli* network. More importantly, all minimal reactions sets identified include 11 of 12 reactions whose corresponding gene deletions were determined experimentally to be lethal for growth on glucose. Earlier analyses based on single gene deletions conducted with this model using linear optimization identified only 7 of 12 lethal gene deletions motivating the importance of considering simultaneous gene deletions within an MILP framework.

In the second case study, the uptake or secretion of any organic metabolite is enabled. The amount of organic material entering the network is kept consistent with the first case study by allowing the uptake of a constrained amount of carbon atoms (<60 mmol/gDW·hr). Unconstrained uptake routes for oxygen, inorganic phosphate, sulfate, and ammonia are also provided as in the first study. Under these "ideal" uptake conditions, we find that a maximum growth rate (MGR) of 1.341 g biomass/gDW·hr is attainable requiring at least 201 metabolic reactions. The fact that only five amino acids are imported under maximum growth (i.e., MGR) conditions indicates that it is stoichiometrically more favorable to produce most amino acids internally rather than transport them into the cell from the medium.

Figure 24:
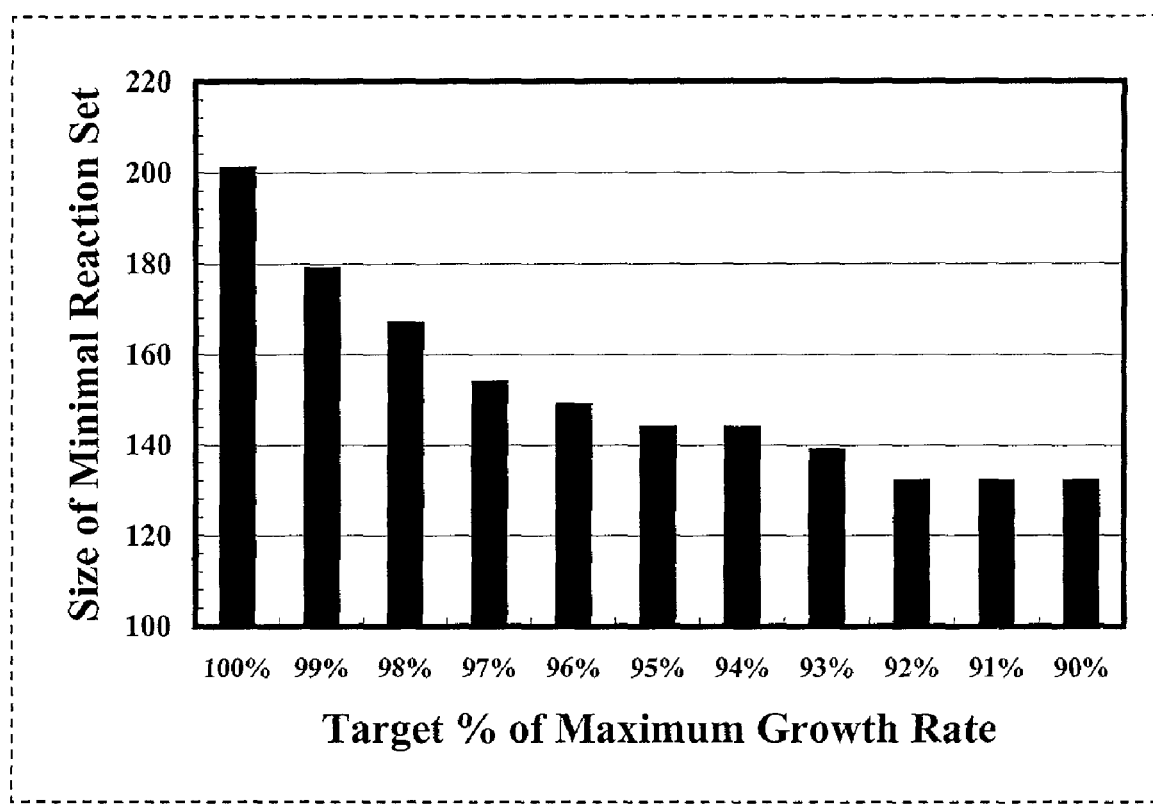
FIGS. 24 and 25 are graphs of a number of reactions in each minimal set as a function of the imposed growth demands for an uptake environments allowing multiple organic uptakes.
Figure 25:
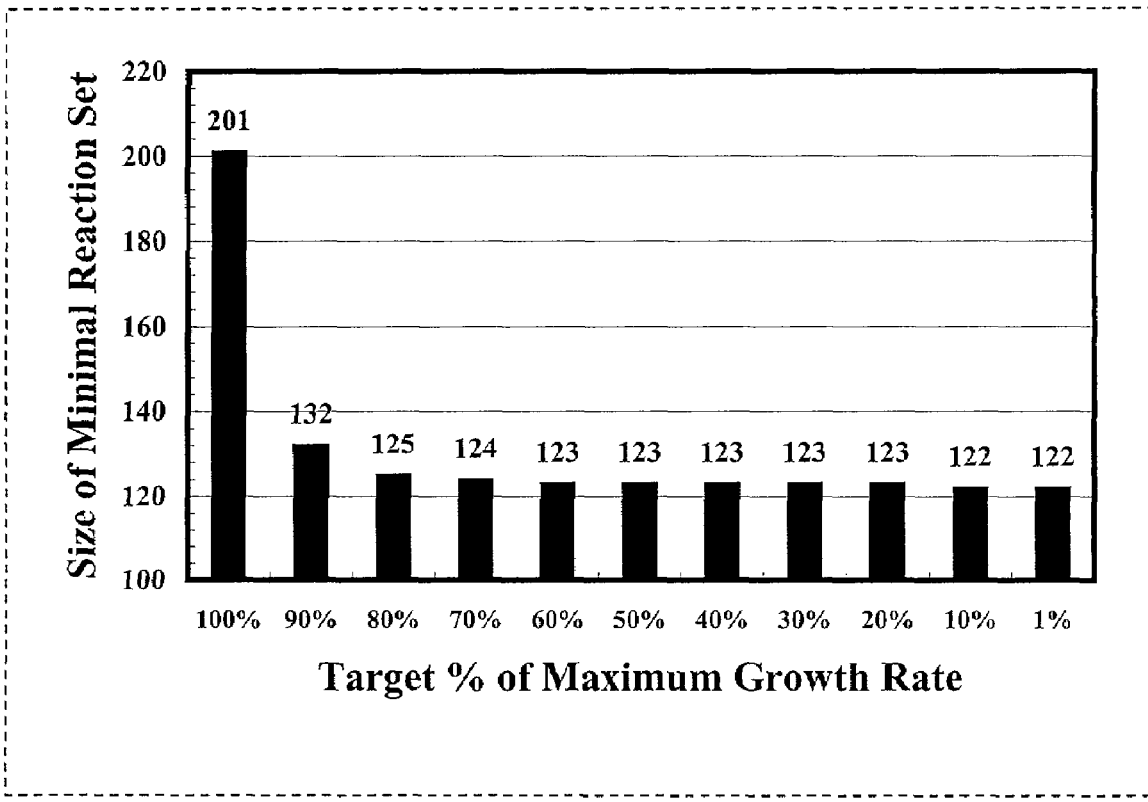

This trend, however, is quickly reversed as the growth rate requirement is reduced. This reversal yields a corresponding sharp decrease in the total number of required reactions as a direct result of the importation of an increasing number of metabolites at sub-maximum target growth demands. The table of FIG. 23 lists the metabolites uptaken or secreted at each target growth rate, while FIG. 24 (100%–90% of MGR) and FIG. 25 (100%–1% of MGR) illustrate the number of required metabolic reactions needed to attain various target growth demands. The rapid reduction in size of the minimal reaction sets by importing an increasing number of metabolites as the biomass demands are lessened (see FIG. 23) continues until the growth demands are reduced to about 90% from the MGR. Below this growth target (see FIG. 25) additional but modest reductions are achieved primarily through flux redirections. FIG. 26 summarizes the reactions which are being removed or added to the minimal reaction set as the growth target is successively lowered. The smallest minimal reaction network for the second case study, comprised of 122 reactions, is reached when the target growth demands are lowered to 10% of the MGR. This minimal network is comprised mostly of cell envelope and membrane lipid biosynthetic reactions, along with a number of transport and salvage pathway reactions, as shown in FIG. 27. As in the glucose-only study, multiple minimal reaction sets for multi-organic uptake case are expected.

9.2 Discussion

In this study, we have identified the minimum number of $E.$ $coli$ metabolic reactions capable of supporting growth under two different uptake environments (i) a glucose or acetate-only uptake environment and (ii) free uptake or secretion of any organic metabolite involving a corresponding transport reaction. The obtained results quantitatively demonstrate that minimal reaction sets and thus corresponding minimal gene sets are strongly dependent on the uptake opportunities afforded by the growth medium. While an $E.$ $coli$ cell grown on a medium containing only glucose or acetate requires at least 224 or 229 metabolic reactions respectively to support growth, a cell cultured on a rich optimally engineered medium could theoretically support growth with as few as 122 metabolic reactions. In addition, the choice of the single substrate affects the minimal reaction set size and composition. As expected, the minimal reaction set becomes larger by increasing the required growth rate. However, the magnitude of this increase is quite different for the examined cases. While in case (i) the minimal reaction set increases only from 224 to 234 to meet the maximum growth rate on glucose and from 229 to 231 for acetate growth, in case (ii) the minimal reaction set almost doubles going from 122 to 201. Another significant observation is the large redundancy of the $E.$ $coli$ metabolic network, which is capable of supporting growth utilizing only 31% of the available metabolic reactions for growth on glucose, and only 17% of the available reactions for growth on a complex medium. Even these reduced minimal reaction network sets exhibit large multiplicities. Specifically, a non-exhaustive list of 100 alternative minimal reaction sets were identified for the glucose-only uptake case.

It must be noted that our analysis provides a species-specific minimal metabolic reaction set, which is a subset of the complete $E.$ $coli$ minimal genome. This is a consequence of the adopted reaction-based analysis which cannot account for genes associated with translation, replication, recombination, repair, transcription, and genes of unknown function. A comparison of our minimal metabolic reaction set with the essential gene set of Hutchison et al. and the minimal gene set proposed by Mushegian and Koonin in their studies with $Mycoplasma\ genitalium$ is provided in FIG. 28. The obtained results agree conceptually with the finding of Hutchison and coworkers (2) that limited metabolic capacity can be compensated for by a proportionately greater dependence on the importation of nucleosides, amino acids, and other metabolites. Although a complete genome-based reconstruction of the $M.$ $genitalium$ metabolic network is currently unavailable preventing a reaction-by-reaction comparison, the distributions of metabolic genes/reactions among the various functional classifications in the three studies are quite similar. Thus, perhaps the simultaneous reaction removal strategy applied to $E.$ $coli$ in this work parallels the evolutionary pressures placed on $M\ genitalium$ to reduce its genome size. The minimal reaction set size overestimation in our analysis may be largely due to its species-specific nature. Whereas the cellular envelope of $E.$ $coli$ contains a cell wall made up largely of peptidoglycan, the cellular envelope of mycoplasmas lacks a cell wall. Thus many of the cellular envelope reactions necessary for $E.$ $coli$ survival are not included in the genes sets of Hutchison et al. and that of Mushegian and Koonin. Another contributing factor is that we assign a different reaction/gene to the uptake or secretion of each metabolite although similar metabolites can be transported by mechanisms associated with a single gene. Furthermore, since our analysis is based on the $E.$ $coli$ model, more efficient reaction combinations, perhaps occurring in non-$E.$ $coli$ species, could further reduce the minimal gene set lowering the discrepancy.

This framework can be utilized to construct minimal reaction sets for additional species. By contrasting these minimal sets it could be inferred how minimal reaction sets (metabolic gene sets) compare along different evolutionary branches. Specifically, minimal reaction sets for $M\ genitalium$ and $H.$ $influenza$ could be determined and benchmarked with earlier studies. Additionally, a species independent minimal metabolic reaction set can be pursued by lumping reactions occurring in many different species within a Universal stoichiometric matrix (15,16). As more elaborate models are developed describing elementary functions of minimal cells, more detail can be added to the model. Apart from utilizing this MILP framework for rationally identifying "minimal" metabolic networks, it can also be used to predict in silico lethal gene deletions for different organisms and uptake environments. By identifying lethal gene deletions for pathogenic microbes (e.g., $H.$ $pylori$), a ranked list of promising targets for therapeutic intervention (i.e., interruption of gene expression) can be compiled. Even though the proposed computational procedure is dependent upon the assumptions of the adopted FBA model, it affords the versatility to study different uptake/secretion environments as well as encompass reaction sets from multiple species in the search for the minimal genome.

9.3 Modeling and Computational Protocol

Flux balance analysis relies on the stoichiometry of biochemical pathways and cellular composition information to identify the flux distributions potentially available to the cell. For a metabolic network comprised of N metabolites and M metabolic reactions we have, $$\frac{dX_i}{dt} = \sum_{j=1}^{M} S_{ij} v_j, i = 1, \ldots, N$$

where $X_i$ is the concentration of metabolite i, $S_{ij}$ is the stoichiometric coefficient of metabolite i in reaction j, and $v_j$ represents the flux of reaction j. Typically, the resulting system of equations is underdetermined (the number of reactions exceeds the number of metabolites). The maximization of growth rate is sometimes employed as a surrogate for cell fitness. The key assumption is that the cell is capable of spanning all flux combinations allowable by the stoichiometric constraints and thus achieving any flux distributions that maximize a given metabolic objective. This may overestimate the region of accessible fluxes by neglecting kinetic and/or regulatory constraints. The optimization model (linear programming) for maximizing biomass production or equivalently growth rate (assuming a 1 gDW·hr basis) is:

$$\text{Maximize } Z = v_{biomass}$$

$$\sum_{j=1}^{M} S_{ij} v_j = b_i, i = 1, \ldots, N$$

$$v_j \in \Re^+, j = 1, \ldots, M$$

$$b_i \in \Re, i = 1, \ldots, N$$

where $v^{biomass}$ is the corresponding reaction flux comprised of all necessary components of biomass in their respective ratios. One gram of biomass is produced per unit flux of $v_{biomass}$. Variable $b_i$ quantifies the uptake (negative sign) or secretion (positive sign) of metabolite i. In case (i), only ammonia, glucose, oxygen, phosphate, and sulfate are allowed to have a negative value for $b_i$ and any metabolite with a transport reaction out of the cell can be secreted, while in case (ii) all organic metabolites can be imported. In this study we explore what is the minimum number of metabolic reactions capable of maintaining maximum and sub-maximal levels of biomass production. By mapping reactions to their corresponding genes a connection between biomass production and gene expression is established. The presence/absence of reactions, and therefore genes, is described mathematically by incorporating logic 0-1 variables into the flux balance analysis framework. These binary variables, $$y_j = \begin{cases} 1 \\ 0 \end{cases}, j = 1, \ldots, M$$

j=1, . . . ,M assume a value of one if reaction j is active and a value of zero if it is inactive. The following constraint, $$v^{min}_j \cdot y_j \leq v_j \leq v^{max}_j \cdot y_j, j=1, \ldots, M$$

ensures that reaction flux $v_j$ is set to zero when no gene coding for the enzyme catalyzing reaction j is present and functional. Alternatively, when such a gene is active, $v_j$ is free to take values between a lower bound $^{min}_j$ and an upper bound $^{max}_j$. The mixed-integer linear programming problem of minimizing the total number of functional reactions in the network capable of meeting a target for biomass production $v^{target}_{biomass}$ is as follows:

$$\text{Minimize } Z = \sum_{j=1}^{M} y_j$$

$$\text{subject to } \sum_{j=1}^{M} S_{ij} v_j = b_i, i = 1, \ldots, N$$

$$v_{biomass} \geq v^{target}_{biomass}$$

-continued $$v^{min}_j \cdot y_j \leq v_j \leq v^{max}_j \cdot y_j, j = 1, \ldots, M$$

$$y_j \in \{0, 1\}, j = 1, \ldots, M$$

$$v_j \in \Re^+, j = 1, \ldots, M$$

$$b_i \in \Re, i = 1, \ldots, N$$

The above MILP belongs to the class of generalized network problems. Here each metabolite constitutes a node and each reaction represents an arc in the network.

The presence of over one thousand binary variables causes the problem to become computationally intractable for some instances. In particular, the computational burden increases for lower biomass targets and it is much greater for case (ii) than case (i) due to the added complexity associated with multiple uptakes. To alleviate the computational burden, four preprocessing techniques are employed: (i) isoenzyme grouping, (ii) futile cycle exclusion, (iii) flux bounds generation, and (iv) connectivity constraint addition. Isoenzyme grouping refers to the aggregation of the 171 reactions catalyzed by isoenzymes. Reactions differing only in the catalyzing enzyme (i.e., isoenzymes) are grouped together treating all isoenzymes as a single reaction. This reduces complexity by pruning the total number of binary variables. Futile cycle exclusion addresses the removal of sets of reactions (2 or more) which collectively recycle fluxes in a loop without any net effect on metabolism. A special case is reversible reactions with nonzero fluxes for both directions. In general, a set K composed of K reactions forms a futile cycle if $$\sum_{j \in K} S_{ij} = 0, i = 1, \ldots, N$$

The following constraint ensures that at least one of them will be inactive breaking the cycle.

$$\sum_{j \in K} y_j \leq K - 1$$

Overall, 346 futile cycles were identified and eliminated from the model. Most of the futile cycles involved simply reversible reactions.

The solution time of the resulting MILP problems is highly dependent on the tightness of the imposed lower $^{min}_j$ and upper $^{max}_j$ bounds on the fluxes $v_j$. Tight bounds $^{min}_j$ and $^{max}_j$ are obtained by minimizing and maximizing respectively, every single reaction flux $v_j$ subject to the flux balance constraints and the biomass target specification.

$$\text{Maximize/Minimize } v_{j^*}$$

$$\text{subject to } \sum_{j=1}^{M} S_{ij} v_j = b_i, i = 1, \ldots, N$$

$$v_{biomass} \geq v^{target}_{biomass}$$

$$v_j \in \Re^+, j = 1, \ldots, M$$

$$b_i \in \Re, i = 1, \ldots, N$$

This is a linear programming (LP) problem (no binary variables) and is quickly solved (i.e., less than a few seconds) for all cases. Note that different bounds are generated for different biomass targets, and the higher the biomass target is, the tighter the obtained bounds are.

Connectivity constraints are also added to ensure that if a reaction producing an intracellular metabolite is active, then at least one reaction consuming this metabolite must be active and vice versa. In addition, if a reaction transporting an extracellular metabolite into the cell is active, then at least one intracellular reaction consuming this metabolite must be active and vice versa. These relations are incorporated in the model as follows after partitioning the reaction set J into two subsets: $J_{int}$ representing intracellular reactions and $J_{trans}$ representing reactions transporting metabolites to and from the cell. The metabolite set I is also partitioned into two subsets with $I_{int}$ and $I_{ext}$ representing intracellular and extracellular metabolites respectively.

$$y_{j'} \leq \sum_{\substack{S_{ij}<0 \\ j \in J}} y_j \; \forall \; i \in I_{int}, \; \forall \; j' \in \{j \mid S_{ij} > 0\} \quad (10)$$

$$y_{j''} \leq \sum_{\substack{S_{ij}>0 \\ j \in J}} y_j \; \forall \; i \in I_{int}, \; \forall \; j'' \in \{j \mid S_{ij} < 0\} \quad (11)$$

$$y_{j'} \leq \sum_{\substack{S_{ij}<0 \\ j \in J_{trans}}} y_j \; \forall \; i \in I_{ext}, \; \forall \; j' \in \{j \mid S_{ij} > 0\} \quad (12)$$

$$y_{j''} \leq \sum_{\substack{S_{ij}>0 \\ j \in J_{trans}}} y_j \; \forall \; i \in I_{ext}, \; \forall \; j'' \in \{j \mid S_{ij} < 0\} \quad (13)$$

These connectivity constraints are also employed to identify the smallest set of reactions capable of ensuring adequate connectivity between the external metabolites and the components of biomass. This problem involves minimizing $$\sum_j y_j$$

subject to constraints (10-13) with an active biomass reaction, $y_{biomass}=1$.

The iterative generation of the multiple minimal reaction sets is achieved by accumulating integer cuts and resolving the MILP formulation. Each integer cut excludes one previously found solution. For example, solution $y_j^*$ is excluded from consideration by adding the following integer cut:

$$\sum_{j \mid y_j^*=1} y_j + \sum_{j \mid y_j^*=0} (1 - y_j) \leq M - 1$$

All optimization problems are solved using CPLEX 6.5 accessed through the modeling environment GAMS on an IBM RS6000-270 workstation. The total cumulative CPU expended for this study was in the order of 400 hours.

10. Options and Variations

The present invention contemplates any number of ways in which the modeling framework of the present invention can be applied to solve metabolic network problems. The framework of the present invention uses a systematic approach to improve upon flux balance models using qualitative information such as can be used to define logic constraints. This information can include qualitative kinetic information constraints, qualitative regulatory information constraints, differential DNA microarray experimental data constraints, and other logic constraints.

The modeling framework of the present invention can be applied to solve various metabolic problems. This includes determining the effect of gene additions and/or deletions, determining optimal gene additions, determining lethal gene deletions, determining minimal reaction sets as well as determining other metabolic manipulations. These and other problems may included requirements of a particular growth rate, certain environmental conditions, or other conditions.

As the modeling framework of the present invention is in silico, it is not limited in any way to a particular organism. The present invention contemplates that any number of organisms can be modeled. The spirit and scope of the invention should be construed broadly to include all that is claimed and any equivalents thereof.

What is claimed is:

1. A method for modeling cellular metabolism of an organism, comprising:
constructing on a computer a flux balance analysis model utilizing stoichiometric mass balances of metabolic and cellular composition information of the organism to identify stoichiometric boundaries for available flux distributions of a metabolic network;
applying logic constraints comprising a regulation matrix to the flux balance analysis model to produce an altered flux balance analysis model, wherein said logic constraints constrain one of said identified stoichiometric boundaries for one of said available flux distributions, wherein said altered flux balance analysis model has improved predictive capabilities of cellular metabolism of the organism over said flux balance analysis model and thereby provides a model of cellular metabolism of the organism; and
providing an output to a user of said available flux distribution having said constrained stoichiometric boundary.

2. The method of claim 1 wherein the logic constraints are capable of protecting against violation of a kinetic barrier.

3. The method of claim 1 wherein the logic constraints further include a set of connectivity restraints.

4. The method of claim 1 further comprising the step of applying mixed-integer linear programming to said altered flux balance analysis model having improved predictive capabilities to solve for a desired metabolic outcome.

5. The method of claim 1 further comprising the step of solving for a desired metabolic outcome.

6. The method of claim 1 wherein the logic constraints further include qualitative regulatory information constraints.

7. The method of claim 6 wherein the logic constraints protect against violation of a regulatory barrier.

8. The method of claim 1 wherein the logic constraints further include DNA microarray experimental data constraints.

9. A method for modeling cellular metabolism of an organism that improves upon a flux balance analysis model, comprising:
constructing on a computer the flux balance analysis model utilizing stoichiometric mass balances of metabolic and cellular composition information of the organism to identify stoichiometric boundaries for available flux distributions of a metabolic network;

applying a plurality of logic constraints comprising a regulation matrix to the flux balance analysis model to produce an altered flux balance analysis model, wherein said plurality of logic constraints constrain one of said identified stoichiometric boundaries for one of said available flux distributions, wherein said altered flux balance analysis model has improved predictive capabilities of cellular metabolism of the organism over said flux balance analysis model and thereby provides a model of cellular metabolism of the organism; and providing an output to a user of said available flux distribution having said constrained stoichiometric boundary.

10. The method of claim 9, further comprising selecting the set of logic constraints to protect against violation of a kinetic or regulatory barrier.

11. The method of claim 9 wherein the logic constraints are defined by a relationship between changes in reaction fluxes and metabolic concentrations.

12. The method of claim 9 wherein the logic constraints are represented by binary variables.

13. The method of claim 12 wherein a first binary variable represents the presence of a reaction and a second binary variable represents the absence of a reaction.

14. The method of claim 9 further comprising applying a computational procedure to identify a minimal set of metabolic reactions.

15. The method of claim 14 further comprising selecting a growth rate, and wherein the step of applying a computational procedure is applying a computational procedure to identify the minimal set of metabolic reactions capable of supporting the growth rate.

16. The method of claim 9 further comprising the step of applying mixed-integer linear programming to said altered flux balance analysis model having improved predictive capabilities to solve for a desired metabolic outcome.

17. The method of claim 9 further comprising the step of solving for a desired metabolic outcome.

18. The method of claim 17 further comprising engineering a change in an organism to produce the desired metabolic outcome.

19. A system for modeling cellular metabolism of an organism, comprising:
a flux balance analysis model utilizing stoichiometric mass balances of metabolic and cellular composition information of the organism to identify stoichiometric boundaries for available flux distributions of a metabolic network;
a plurality of logic constraints comprising a regulation matrix applied to the flux balance analysis model, the logic constraints selected from the set consisting of qualitative kinetic information constraints, qualitative regulatory information constraints, and differential DNA microarray experimental data constraints; and
commands for execution on a computer for producing an altered flux balance analysis model wherein said plurality of logic constraints constrain one of said identified stoichiometric boundaries for one of said available flux distributions, wherein said altered flux balance analysis model has improved predictive capabilities of cellular metabolism of the organism over said flux balance analysis model and thereby provides a model of cellular metabolism of the organism.

20. The system of claim 19, wherein said constraints comprise qualitative kinetic information constraints.

21. The system of claim 19, wherein said constraints comprise qualitative regulatory information constraints.

22. The system of claim 19, wherein said constraints comprise differential DNA microarray experimental data constraints.

23. A method for modeling cellular metabolism of an organism, comprising:
constructing on a computer a flux balance analysis model of a metabolic network of the organism;
applying constraints to the flux balance analysis model, wherein the constraints include qualitative kinetic information constraints, qualitative regulatory information constraints, differential DNA microarray experimental data constraints, or a combination thereof;
producing an altered flux balance analysis model wherein said constraints constrain a stoichiometric boundary for an available flux distribution, wherein said altered flux balance analysis model has improved predictive capabilities of cellular metabolism of the organism over said flux balance analysis model and thereby provides a model of cellular metabolism of the organism; and
providing an output to a user of said available flux distribution having said constrained stoichiometric boundary.

24. The method of claim 23 wherein the constraints include logic constraints to protect against violation of a regulatory barrier.

25. The method of claim 23 wherein the constraints further include connectivity restraints.

26. The method of claim 23 further comprising applying mixed-integer linear programming to said altered flux balance analysis model having improved predictive capabilities to solve for a desired metabolic outcome.

27. The method of claim 23 further comprising solving for a desired metabolic outcome.

28. The method of claim 23, wherein said constraints include qualitative kinetic information constraints.

29. The method of claim 23, wherein said constraints include qualitative regulatory information constraints.

30. The method of claim 23, wherein said constraints include differential DNA microarray experimental data constraints.

31. A method for modeling cellular metabolism of an organism that improves upon a flux balance analysis model, comprising:
constructing on a computer the flux balance analysis model utilizing stoichiometric mass balances of metabolic and cellular composition information of the organism to identify stoichiometric boundaries for available flux distributions of a metabolic network;
applying a plurality of logic constraints comprising a regulation matrix to the flux balance analysis model to produce an altered flux balance analysis model, wherein said plurality of logic constraints constrain one of said identified stoichiometric boundaries for one of said available flux distributions, wherein said altered flux balance analysis model has improved predictive capabilities of cellular metabolism of the organism over said flux balance analysis model; applying mixed-integer linear programming to said altered flux balance analysis model having improved predictive capabilities to solve for a desired metabolic outcome of the altered flux balance analysis model, thereby modeling cellular metabolism of the organism; and
providing an output to a user of the application of mixed-integer linear programming to solve for a desired metabolic outcome.

32. The method of claim 31 further comprising the step of solving for the desired metabolic outcome.

33. The method of claim 32 further comprising engineering a change in the organism to produce the desired metabolic outcome.

34. A method for modeling cellular metabolism of an organism, comprising:

constructing on a computer a flux balance analysis model using stoichiometric mass balances of metabolic and cellular composition information of the organism to identify stoichiometric boundaries for available flux distributions of a metabolic network;

determining logic constraints comprising a regulation matrix to apply to the flux balance analysis model, the logic constraints based on qualitative relationships between changes in reaction fluxes and changes in metabolite concentrations;

applying the logic constraints to the flux balance analysis model to produce an altered flux balance analysis model, wherein said logic constraints constrain one of said identified stoichiometric boundaries for one of said available flux distributions, wherein said altered flux balance analysis model has improved predictive capabilities of cellular metabolism of the organism over said flux balance analysis model and thereby provides a model of cellular metabolism of the organism; and providing an output to a user of said available flux distribution having said constrained stoichiometric boundary.

* * * * *

UNITED STATES PATENT AND TRADEMARK OFFICE
CERTIFICATE OF CORRECTION

PATENT NO. : 7,711,490 B2
APPLICATION NO. : 10/043440
DATED : May 4, 2010
INVENTOR(S) : Costas D. Maranas et al.

It is certified that error appears in the above-identified patent and that said Letters Patent is hereby corrected as shown below:

Col 1, Line 11:

ADD
--GRANT REFERENCE
This invention was made with government support under Grant No. CTS9701771, awarded by the National Science Foundation. The Government has certain rights in the invention.--

Signed and Sealed this

Twenty-second Day of June, 2010

David J. Kappos
*Director of the United States Patent and Trademark Office*